United States Patent
Kashkarov et al.

(10) Patent No.: US 8,317,818 B2
(45) Date of Patent: Nov. 27, 2012

(54) REMOVABLE BLOOD CLOT FILTER WITH EDGE FOR CUTTING THROUGH THE ENDOTHELIUM

(75) Inventors: Alexander Germanovich Kashkarov, St. Petersburg (RU); Andrzej J. Chanduszko, Chandler, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/096,893

(22) PCT Filed: Dec. 29, 2006

(86) PCT No.: PCT/US2006/062722
§ 371 (c)(1),
(2), (4) Date: Mar. 23, 2009

(87) PCT Pub. No.: WO2007/079409
PCT Pub. Date: Jul. 12, 2007

(65) Prior Publication Data
US 2009/0209996 A1 Aug. 20, 2009

Related U.S. Application Data

(60) Provisional application No. 60/754,600, filed on Dec. 30, 2005.

(51) Int. Cl.
*A61F 2/01* (2006.01)
(52) U.S. Cl. ........................................................ 606/200
(58) Field of Classification Search .................. 606/200
See application file for complete search history.

(56) References Cited

U.S. PATENT DOCUMENTS

| | | | |
|---|---|---|---|
| 4,425,908 A | 1/1984 | Simon | |
| 4,494,531 A | 1/1985 | Gianturco | |
| 4,688,553 A | 8/1987 | Metals | |
| 5,108,418 A | 4/1992 | Lefebvre | |
| 5,669,933 A | 9/1997 | Simon et al. | |
| 5,709,704 A | 1/1998 | Nott et al. | |
| 5,776,162 A | 7/1998 | Kleshinski | |
| 5,800,457 A | 9/1998 | Gelbfish | |
| 5,836,968 A | 11/1998 | Simon et al. | |
| 5,836,969 A * | 11/1998 | Kim et al. ................. | 606/200 |
| 6,007,558 A * | 12/1999 | Ravenscroft et al. ....... | 606/200 |
| 6,080,178 A | 6/2000 | Meglin | |

(Continued)

FOREIGN PATENT DOCUMENTS
EP    188927 B1    7/1989
(Continued)

OTHER PUBLICATIONS

International Search Report, PCT/US2006/062722.
(Continued)

*Primary Examiner* — Elizabeth Houston
*Assistant Examiner* — Sarah Webb
(74) *Attorney, Agent, or Firm* — Garvey, Smith, Nehrbass & North, L.L.C.; Charles C. Garvey, Jr.; Seth M. Nehrbass

(57) ABSTRACT

A removable blood clot filter includes anchor members with a sharp edge configured so that when the filter is removed the sharp edge aids in passing the anchor members through endothelial tissue. The filter may also include a sharp edge on locator members configured to aid pulling the locator members away from the endothelial tissue.

13 Claims, 19 Drawing Sheets

U.S. PATENT DOCUMENTS

| | | |
|---|---|---|
| 6,156,055 A | 12/2000 | Ravenscroft |
| 6,176,871 B1 | 1/2001 | Pathak et al. |
| 6,193,739 B1 | 2/2001 | Chevillon et al. |
| 6,258,026 B1 | 7/2001 | Ravenscroft et al. |
| 6,267,776 B1 | 7/2001 | O'Connell |
| 6,273,900 B1 | 8/2001 | Nott et al. |
| 6,331,183 B1 | 12/2001 | Suon |
| 6,436,120 B1 | 8/2002 | Meglin |
| 6,443,972 B1 | 9/2002 | Bosma et al. |
| 6,468,290 B1 | 10/2002 | Weldon et al. |
| 6,540,767 B1 | 4/2003 | Walak et al. |
| 6,589,266 B2 | 7/2003 | Whitcher et al. |
| 6,623,506 B2 | 9/2003 | McGuckin, Jr. et al. |
| 6,872,217 B2 | 3/2005 | Walak et al. |
| 7,056,286 B2 | 6/2006 | Ravenscroft et al. |
| 2001/0003796 A1 | 6/2001 | Yang et al. |
| 2001/0039432 A1 | 11/2001 | Whitcher et al. |
| 2003/0071285 A1 | 4/2003 | Tsukernik |
| 2003/0074019 A1 | 4/2003 | Gray et al. |
| 2003/0187495 A1 | 10/2003 | Cully et al. |
| 2004/0073252 A1 | 4/2004 | Goldberg et al. |
| 2004/0186512 A1 | 9/2004 | Bruckheimer et al. |
| 2004/0193209 A1 | 9/2004 | Pavcnik et al. |
| 2005/0055045 A1 | 3/2005 | DeVries et al. |
| 2005/0085847 A1 | 4/2005 | Galdonik et al. |
| 2005/0159771 A1 | 7/2005 | Petersen |
| 2005/0159773 A1 | 7/2005 | Broome et al. |
| 2005/0163821 A1 | 7/2005 | Sung et al. |
| 2005/0177224 A1 | 8/2005 | Fogarty et al. |
| 2005/0203566 A1* | 9/2005 | Beulke .......................... 606/200 |
| 2005/0234503 A1 | 10/2005 | Ravenscroft et al. |
| 2005/0277977 A1 | 12/2005 | Thornton |
| 2006/0036279 A1 | 2/2006 | Eidenschink et al. |
| 2006/0095068 A1 | 5/2006 | WasDyke et al. |

FOREIGN PATENT DOCUMENTS

| | | |
|---|---|---|
| WO | WO 2006/124405 A2 | 11/2006 |
| WO | WO 2007/021340 A1 | 2/2007 |

OTHER PUBLICATIONS

International Preliminary Report on Patentability and Written Opinion of the International Searching Authority in PCT/US06/62722.

* cited by examiner

REMOVABLE BLOOD CLOT FILTER WITH EDGE FOR CUTTING THROUGH THE ENDOTHELIUM

PRIORITY DATA AND INCORPORATION BY REFERENCE

This application claims benefit of priority to U.S. Provisional Patent Application No. 60/754,600, filed Dec. 30, 2005 which is incorporated by reference in its entirety. This invention is related to the subject matter shown and described in the following: (i) PCT International Application No. PCT/US06/62733, filed Dec. 29, 2006, entitled "Embolus Blood Clot Filter Removal System and Method," and claiming the benefit of priority to U.S. Provisional Patent Application No. 60/754,598, filed Dec. 30, 2005; (ii) PCT International Application No. PCT/US06/62719, filed Dec. 29, 2006, entitled "Embolus Blood Clot Filter with Post Delivery Actuation," and claiming the benefit of priority to U.S. Provisional Patent Application No. 60/754,633, filed Dec. 30, 2005; (iii) PCT International Application No. PCT/US06/62725, filed Dec. 29, 2006, entitled "Embolus Blood Clot Filter Delivery System," and claiming the benefit of priority to U.S. Provisional Patent Application No. 60/754,636, filed Dec. 30, 2005; (iv) PCT International Application No. PCT/US06/62720, filed Dec. 29, 2006, entitled "Embolus Blood Clot Filter with Floating Filter Basket," and claiming the benefit of priority to U.S. Provisional Patent Application No. 60/754,599, filed Dec. 30, 2005; and (v) PCT International Application No. PCT/US06/62730, filed Dec. 29, 2006, entitled "Embolus Blood Clot Filter with Bio-Resorbable Coated Filter Members," and claiming the benefit of priority to U.S. Provisional Patent Application No. 60/754,597, entitled "Embolus Blood Clot Filter with Retainers on Locator Filter Members," filed Dec. 30, 2005, each of which is hereby incorporated by reference in its entirety.

TECHNICAL FIELD

This invention relates to a filter device that can be placed in a blood vessel to reduce the risk of embolisms and, if needed, removed from the blood vessel without causing traumatic damage to the blood vessel.

BACKGROUND ART

In recent years, a number of medical devices have been designed which are adapted for compression into a small size to facilitate introduction into a vascular passageway and which are subsequently expandable so as to make contact with the walls of the passageway. These devices include, among others, blood clot filters which expand and are held in position by engagement with the inner wall of a blood vessel, such as a vein and in particular the vena cava. These vena cava filters have been designed to remain in place permanently. Such filters include structure to secure the filter within the vena cava, such as elongate diverging anchor members with hooked ends that penetrate the vessel wall and positively prevent longitudinal migration in either direction within the vessel. The hooks on filters of this type are rigid and will not bend, and within two to six weeks after a filter of this type has been implanted, the endothelium layer grows over the diverging anchor members and positively locks the hooks in place. Thereafter, any attempt to remove the filter results in a risk of injury to the vena cava, including potential rupture.

A number of conditions and medical procedures subject the patient to a short term risk of pulmonary embolism which can be alleviated by a filter implant. In such cases, patients are often averse to receiving a permanent implant because the risk of pulmonary embolism may disappear after a period of several weeks or months. However, not all existing filters are conducive to removal after they have been implanted for more than two weeks. Moreover, most existing filters have different consequences on the vessel wall during removal subsequent to the two-week time period. For example, a known filter is believed to cause the vessel wall diameter to collapse substantially upon removal of such filter due to the attachment of the hooks to the vessel wall.

In an attempt to provide a removable filter, two filter baskets have been formed along a central shaft that are conical in configuration, with each basket being formed by spaced struts radiating outwardly from a central hub. The central hubs are held apart by a compression unit, and the locator members of the two baskets overlap so that the baskets face one another. Filters of this type require the use of two removal devices inserted at each end of the filter to draw the baskets apart and fracture the compression unit. The end sections of the locator members are formed to lie in substantially parallel relationship to the vessel wall and the tips are inclined inwardly to preclude vessel wall penetration. If a device of this type is withdrawn before the endothelium layer grows over the locator members, vessel wall damage is minimized. But after the endothelium layer grows over the locators, the combined inward and longitudinal movement of the filter baskets as they are drawn apart can tear this layer.

Filters designed to be removable have been disclosed, such as in U.S. Pat. Nos. 6,007,558 and 6,258,026. These disclosed filters feature anchor members 30 which are fabricated so the hook portion has a cross section smaller than that of the rest of the anchor member, as illustrated in FIGS. 22 and 23A. So configured, when an extraction tool pulls on the filter hub 10, the force is transferred through the anchor member to the hook which, implanted in the vessel wall, preferentially bends as illustrated in FIG. 23B. So bent, the hooks may exit without rupturing the vessel wall. Nevertheless, if the filter has been in the blood vessel for several weeks, the endothelial overgrowth may be substantial enough to be vulnerable to lateral movement of the anchor and hook. As illustrated in FIG. 24, with the hook 40 in a bent configuration, tension 8 along the anchor 30 will result in a lateral force 9 which may tend to rip the hook 40 and lower portion of the anchor through the endothelial overgrowth 7. If the endothelial overgrowth 7 does not easily tear or split, the overgrowth may complicate removal of the filter or the blood vessel may be damaged.

SUMMARY OF THE INVENTION

The various embodiments provide a removable blood filter that allows for removal with minimal injury to the endothelial overgrowth layer by including a sharp edge on the hook and/or anchor positioned to cut or induce a clean tear through the endothelium.

In an embodiment, a filter for placement in blood flow within a blood vessel includes a plurality of filter members. At least one of the filter members includes a sharp edge.

In an embodiment, the anchor members include a hook and a sharp edge is provided on a portion of anchor member and over at least a portion of the hook. The sharp edge may project toward or generally face a longitudinal axis of the filter and thus away from the blood vessel wall. More than one sharp edge may be provided on the anchor member and hook. In another embodiment, one or more of the locator members includes a sharp edge which may project toward or generally face the longitudinal axis of the filter.

In yet a further aspect of the various embodiments, a filter to be placed in a blood vessel includes a hub, a plurality of anchor members and a plurality of locator members. The hub is disposed along a longitudinal axis. The plurality of anchor members branch from the hub. Each anchor includes a hook that: (i) penetrates a wall of the blood vessel, (ii) may be spaced along the longitudinal axis from the hub, and (iii) may be radially spaced from the longitudinal axis a first distance. Each anchor further includes a sharp edge over a portion of the anchor and the hook. The plurality of locators branch from the hub. Each locator includes a base portion proximate the hub, a first portion that extends from the base portion and along a first axis, a second portion that extends from the first portion and along a second axis, which may be distinct from the first axis, and a tip portion that extends from the second portion and along a tip axis, which may be distinct from the first and second axes. The tip portion (i) engages the wall of the blood vessel, (ii) may be spaced along the longitudinal axis from the hub, and (iii) may be radially spaced from the longitudinal axis a second distance, which may be less than the first radial distance. In an embodiment, the tip portion may also include a sharp edge projecting toward the longitudinal axis.

In yet an additional aspect of the various embodiments, a method of making a blood filter includes the step of forming a sharp edge on at least one of the filter members, such as an anchor and/or locator member. The sharp edge may be formed by removing material from the filter member or by adding material. In an embodiment, material may be added by wrapping a foil about the member so the ends of the foil form the sharp edge.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, explain features of the invention.

MODE(S) FOR CARRYING OUT THE INVENTION

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient," "host" and "subject" refer to any human or animal subject and are not intended to limit the systems or methods to human use, although use of the subject invention in a human patient represents a preferred embodiment.

Figure 1:
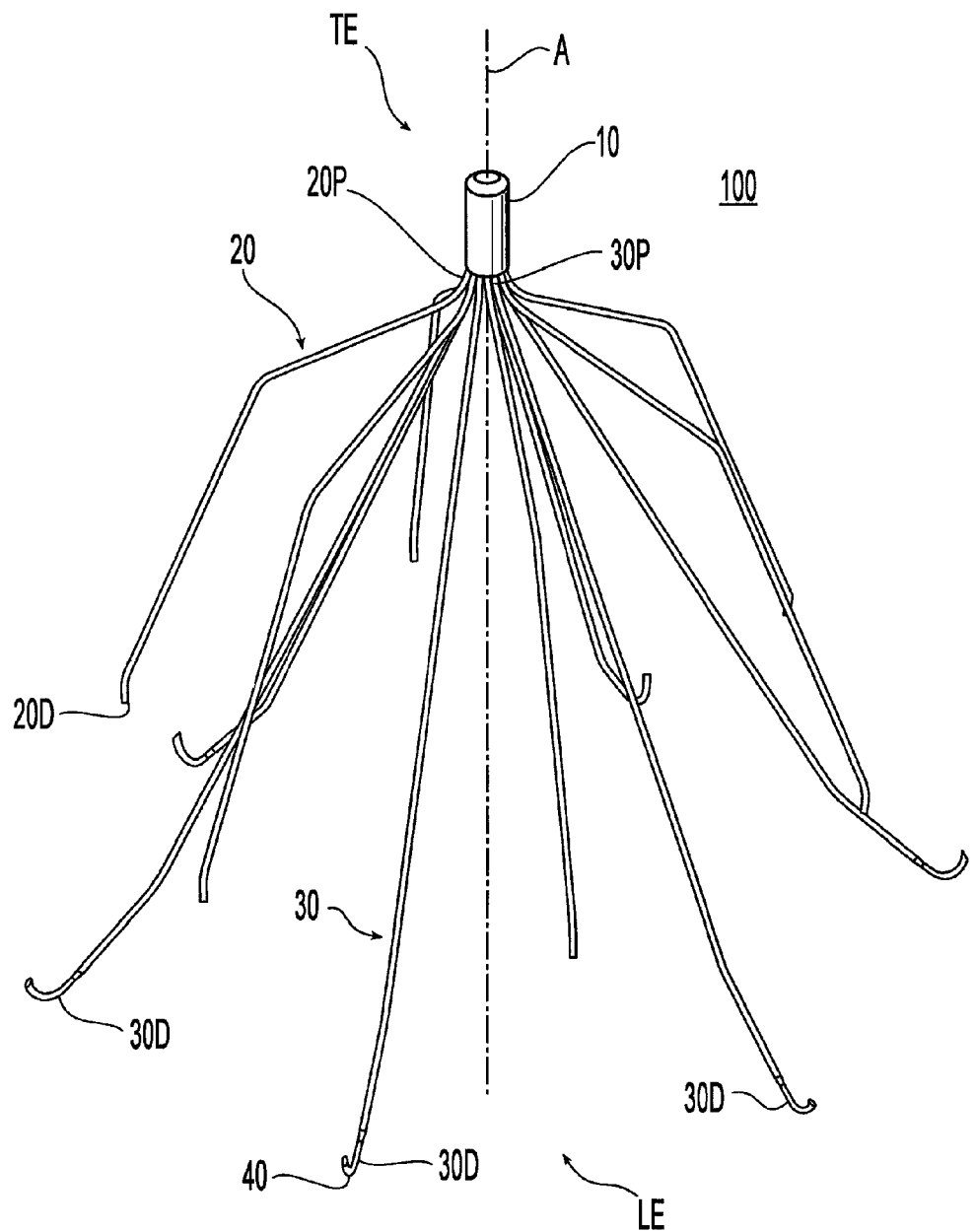
FIG. 1 is a top down perspective view of an embodiment of the blood filter.

Referring to FIG. 1, a filter 100 is illustrated in a perspective view. The filter 100 includes a hub 10, locator members 20, and anchor members 30 with hooks 40. The filter 100 can be made from a plurality of elongate wires, which are preferably metal such as Elgiloy®, stainless steel, or titanium, and more preferably are a super-elastic shape memory alloy, such as Nitinol. The shape memory alloy can further be defined as preferably having an austenite finish (Af) temperature below body temperature. The wires are held together at the filter trailing end by a hub 10 using a suitable connection technique, such as, for example, electrical discharge machining, welding, laser welding, plasma welding or being bonded together. Preferably, the wires are plasma welded. As used herein, "wire" refers to any elongated members of narrow cross section, including rods, bars, tubes, ribbon and narrow sections cut from thin plate. This term is not intended to limit the scope of the invention to elongated members of circular cross section, cut from wire stock or manufactured according to a particular method of metal forming.

Each locator member 20 has a base portion or proximal locator end 20P and a distal locator end 20D. Similarly, each anchor member 30 has a proximal anchor end 30P and a distal anchor end 30D. The distal anchor end 30D may include a hook 40 as shown.

Figure 4A:
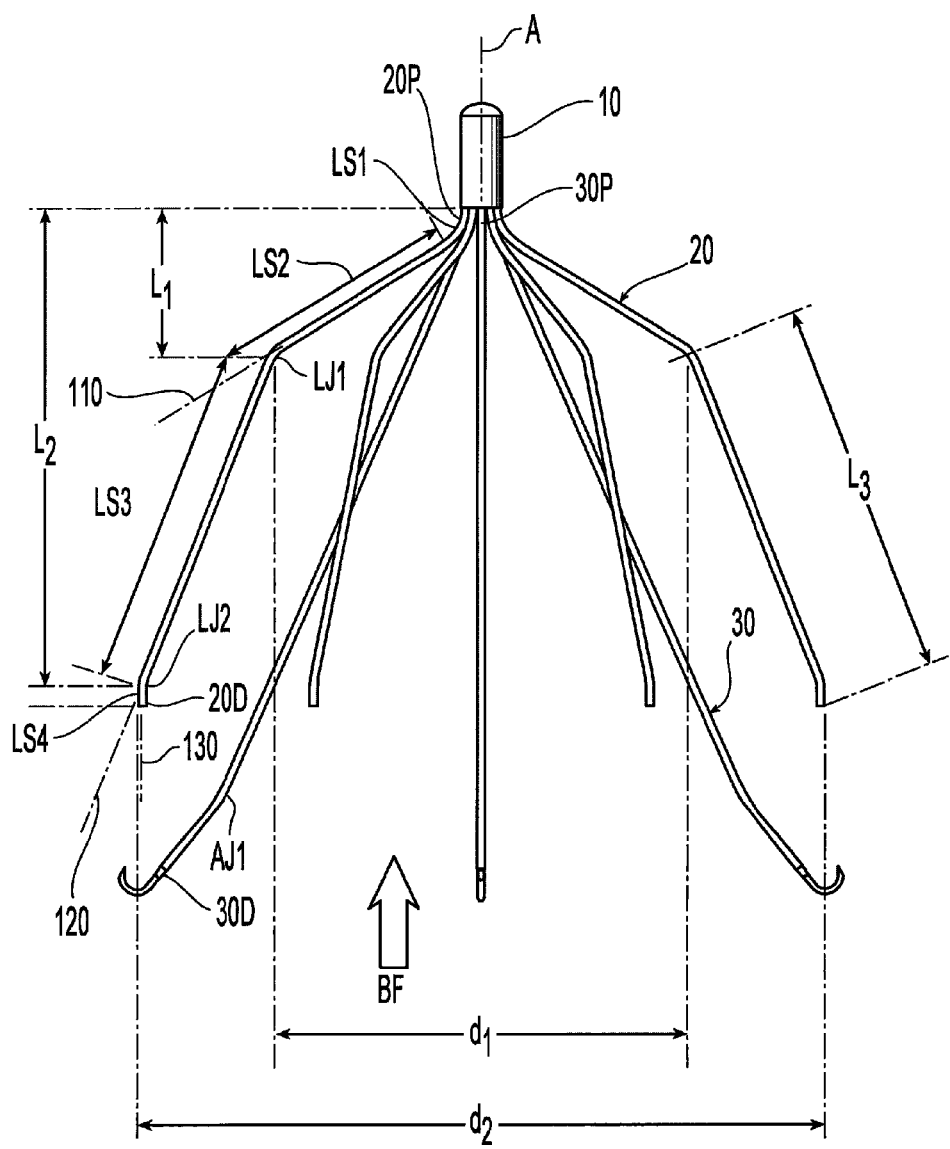
FIG. 4A is a side view of the filter viewed along view IVA-IVA shown in FIG. 3.
Figure 4B:
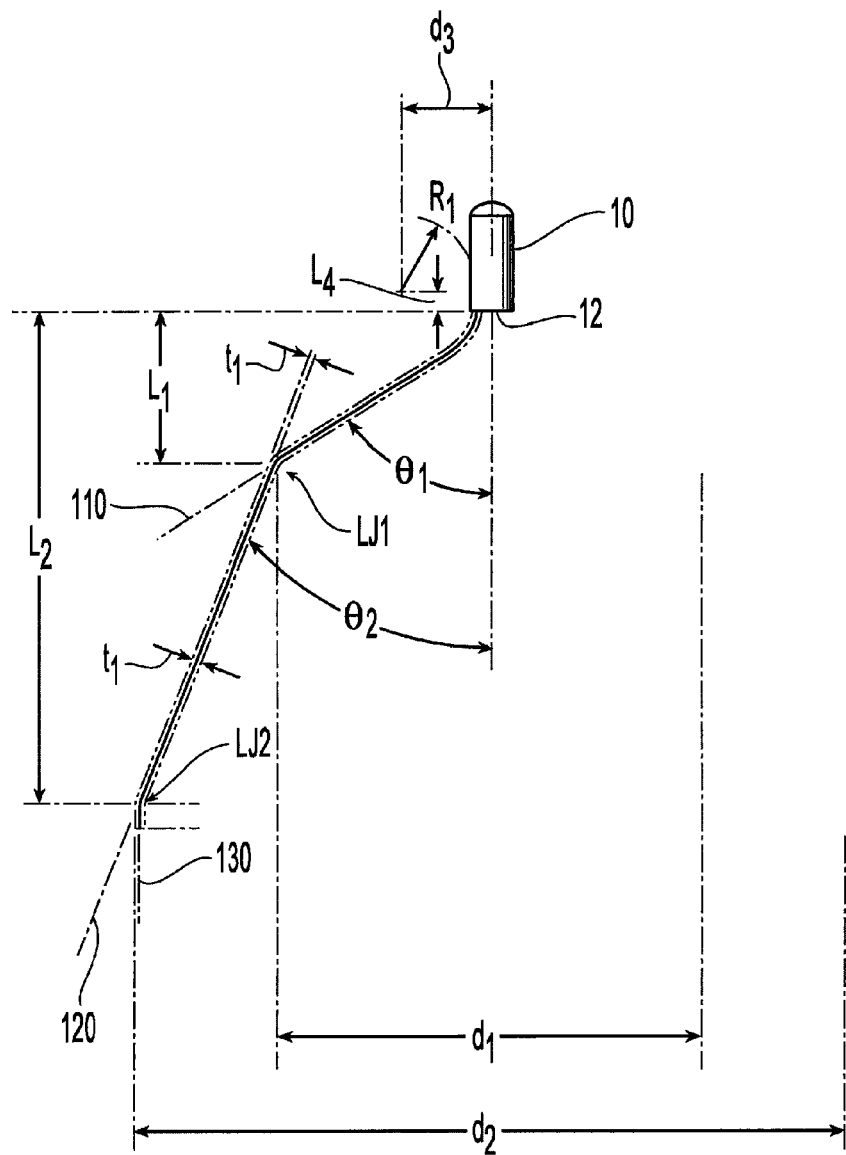
FIG. 4B is a side view of one locator member of the filter of FIG. 1.

Referring to FIGS. 4A and 4B, the locator member 20 may comprise a plurality of locator segments, preferably between 3 and 6 segments and more preferably four locator segments LS1, LS2, LS3, and LS4. First locator segment LS1 may be a curved portion extending from the hub in a first direction along the longitudinal axis A. Second locator segment LS2 may extend generally linearly along a second axis 110 from first locator segment LS1. Third locator segment LS3 preferably extends generally linearly along a third axis 120 from second locator segment LS2, and the fourth locator segment LS4 preferably extends generally linearly along a fourth axis 130 from third locator segment LS3. In a preferred embodiment, the various axes A, 110, 120, 130, and 140 are distinct from one another in that each may intersect with one another but none of them are substantially collinear with each other.

Second locator segment LS2 may be distinct from locator segment LS3 by virtue of a joint or bend LJ1. Third locator segment LS3 may be distinct from locator segment LS4 via a joint or bend LJ2. Joints or bends LJ1 or LJ2 can be viewed as locations formed by the intersection of the segments defining a radiused portion connecting any two segments.

The number of locator members 20 may range from 3 to 12. The filter embodiment illustrated in FIG. 4A includes six locators that are generally equiangularly spaced about axis A. In the embodiment illustrated in FIG. 4B, locator segment LS1 extends through an arc with a radius of curvature $R_1$ whose center may be located along an axis orthogonal to axis A over a radially transverse distance $d_3$ and over a longitudinal distance $L_4$ as measured from a terminal surface 12 of the hub 10 along an axis generally parallel to the longitudinal axis A. Second locator segment LS2 extends along axis 110 to form a first angle $\theta_1$ with respect to the longitudinal axis A whereas locator segment LS3 extends along axis 120 to form second angle $\theta_2$. As shown in FIG. 4B, the first locator joint or bend LJ1 may be located at a longitudinal length $L_1$ generally parallel to axis A from the hub's terminal surface 12. The first locator joint or bend LJ1 may also be located at a distance of about one-half distance $d_1$ from axis A on a generally orthogonal axis with respect to axis A, as shown in FIG. 4A. The distance $d_1$ is preferably the distance between inside facing surfaces of respective diametrically disposed locators 20. The second locator joint LJ2 may be located over a longitudinal length $L_2$ generally parallel to axis A. The second locator joint LJ2 may be located over a distance of about one-half diameter $d_2$ from axis A. The distance $d_2$ is the distance between the outermost surface of the fourth segment LS4 of respective diametrically disposed locators 20. The thickness $t_1$ of locator member 20 where, for example, the locator member 20 is preferably a wire of circular cross section, the thickness $t_1$ of the locator 20 is preferably defined by the diameter of the wire.

A range of values may be used for the aforementioned dimensional parameters in order to provide locator members 20 that will locate the filter within the vein or vessel such that segment LS4 is approximately parallel to the walls of the vein or vessel and provides enough lateral force against the vein or vessel wall to position the filter without injuring the wall. For example, a filter intended to be placed in a narrow vein or vessel, such as a human infant or canine vena cava, may have smaller dimensions $L_1$, $L_2$, $L_3$, $L_4$, LS1, LS2, LS3, LS4, $d_1$ and $d_2$ so that the positioning members can deploy sufficiently to accomplish the positioning and filtering functions, than a filter intended to be placed in a large vein or vessels, such as an adult human vena cava or femoral vein. In an example embodiment suitable for an adult human vena cava filter, when the filter is at the temperature of the subject and unconstrained, the radius of curvature $R_1$ is about 0.02 inches with the center of the radius $R_1$ being located over a distance $d_3$ from the axis A of about 0.1 inches and length $L_4$ of about 0.2 inches; the length $L_1$ may be about 0.3 inches; length $L_2$ may be about 0.9 inches; distance $d_1$ (as measured to the inside facing surfaces of diametrically disposed locators 20) may be about 0.8 inches; distance $d_2$ may be about 1.3 inches; the first angle $\theta_1$ may be about 0 to 90 degrees, the second angle $\theta_2$ may be about 0 to 60 degrees; and the thickness $t_1$ of the locator may be about 0.013 inches. It should be noted that the values given herein are approximate, representing a dimension within a range of suitable dimensions for the embodiments illustrated in the figures, and that any suitable values can be used as long as the values allow the filter to function as intended in a subject's blood vessel.

Figure 5A:
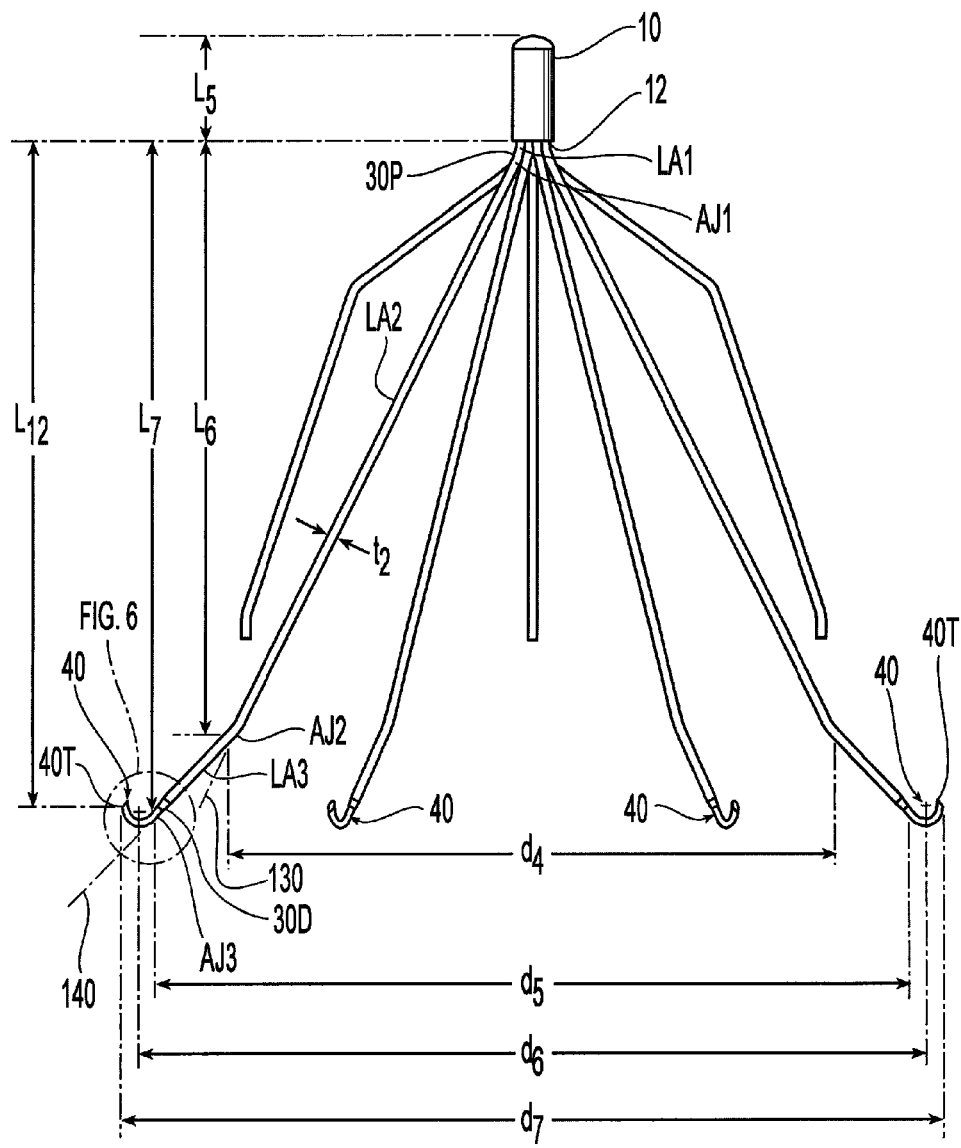
FIG. 5A is a side view of the filter viewed along view VA-VA shown in FIG. 3.
Figure 5B:
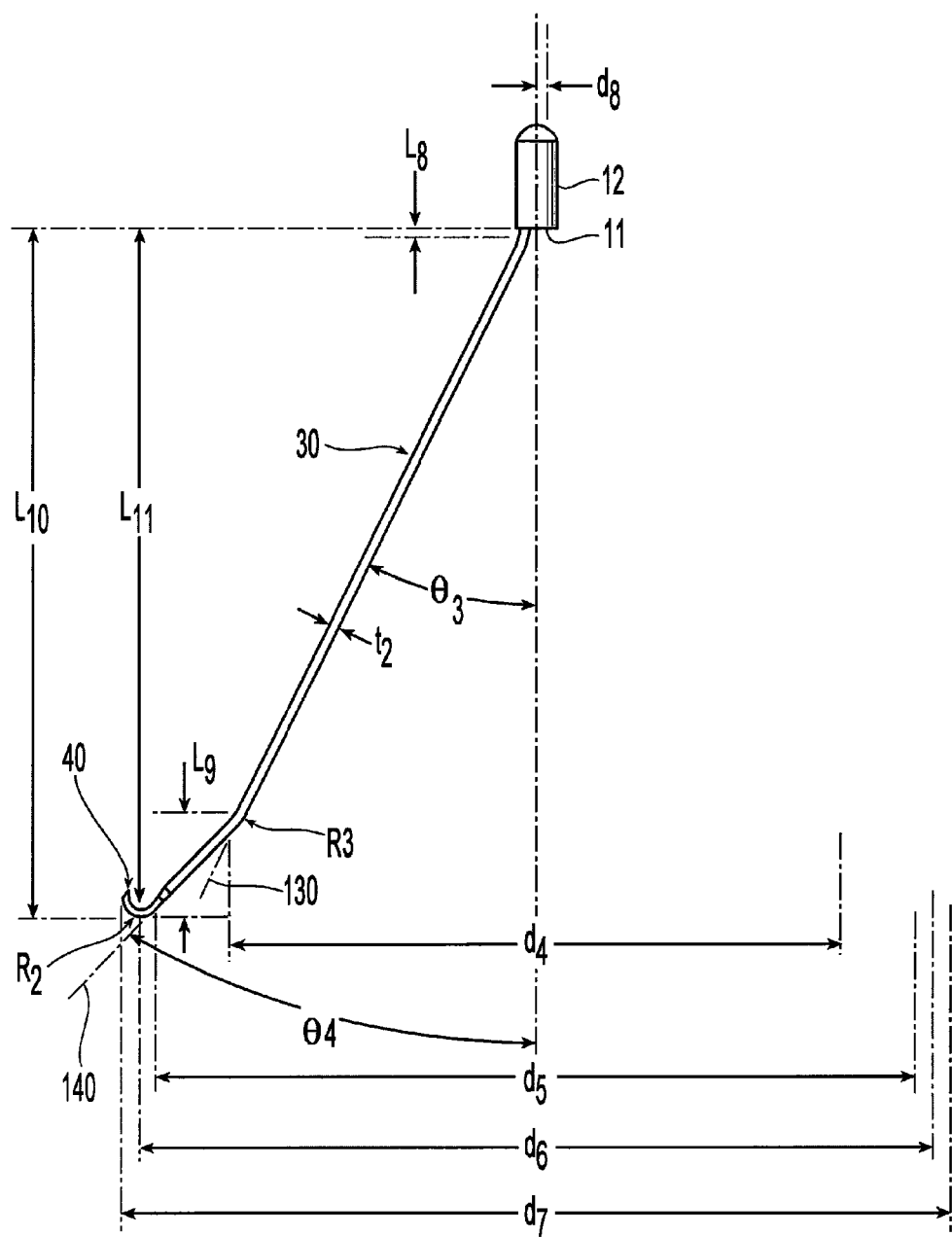
FIG. 5B is a side view of an anchor member of the filter of FIG. 1.

Referring to FIGS. 5A and 5B, the hub 10 may be provided with an internal cylindrical opening with a diameter of about two times the distance $d_8$. Each of the plurality of anchor members 30 may be provided with a first anchor segment LA1, a portion of which is disposed within the hub 10, connected to a second anchor segment LA2 by a first anchor joint or bend AJ1. The second anchor segment LA2 may also be connected to a third anchor segment LA3 via a second anchor joint or bend AJ2, and the third anchor segment LA3 may be connected to a hook 40 via third anchor joint or bend AJ3. The first anchor segment LA1 extends obliquely with respect to axis A. The second anchor segment LA2 extends along axis 130 oblique with respect to the axis A over an angle $\theta_3$ with respect to the longitudinal axis A. The third anchor segment LA3 extends along axis 140 oblique with respect to the longitudinal axis A over an angle $\theta_4$. The second anchor joint or bend AJ2 can be located at a sixth longitudinal distance $L_6$ as measured on an axis generally parallel to the axis A from the terminal surface 12 of the hub 10 and at about one half the fourth distance $d_4$ as measured between generally diametrical end points of two anchors 30 on an axis generally orthogonal to the axis A. The third anchor joint AJ3 may be located at a seventh longitudinal distance $L_7$ as measured along an axis generally parallel to axis A and at a transverse distance of about one-half distance $d_5$ as measured on an axis orthogonal to the axis A between the inner surfaces of two generally diametric anchors 30. The thickness of anchor member 30 is nominally $t_2$. Where the anchor member 30 is a wire of circular cross section, the thickness $t_2$ of the anchor 30 may be the diameter of the wire. As shown in FIG. 5B, the hook 40 may be contiguous to a plane located at a longitudinal distance of $L_{10}$ as measured from the terminal surface 12 of hub 10. The hook 40 may be characterized by a radius of curvature $R_2$, in its expanded configuration at a suitable temperature, e.g., room temperature or the internal temperature of a subject. The center of the hook curvature $R_2$ can be located at a distance $L_{11}$ as measured along an axis generally parallel to the axis A from the terminal surface 12 of hub 10 and at one-half distance $d_6$ as measured between two generally diametrical hooks 40. The tips 40T of respective diametric hooks 40 may be located at longitudinal distance $L_{12}$ (which may be approximately the same as longitudinal distance $L_7$ to the third anchor joint AJ3) and at one half of distance $d_7$ between diametric hooks 40.

A range of values may be used for the aforementioned dimensional parameters in order to provide anchor members 30 that will secure the filter within the vein or vessel such that the hooks 40 are in contact with the walls of the vein or vessel and provide enough lateral force against the walls to ensure the hooks engage, but do not substantially injure, the wall. For example, a filter intended to be placed in a narrow vein or vessel, such as a child or canine vena cava, may have smaller dimensions than a filter intended to be placed in a large vein or vessel, such as an adult vena cava or femoral vein so as to allow the anchor members 30 to adequately deploy and thereby accomplish the positioning, anchoring and filtering functions. In an example embodiment suitable for an adult human vena cava filter, when the filter is at the temperature of the subject and unconstrained, the longitudinal distance or axial length $L_8$ of the first anchor segment LA1 may be about 0.02 inches; the longitudinal distance L9 between the second and third anchor joints AJ2, AJ3 may be about 0.2 inches; $L_{10}$ may be about 1.4 inches; $L_{11}$ may be about 1.4 inches; $d_6$ may be about 1.5 inches; $d_7$ may be about 1.6 inches; $d_8$ may be about 0.01 inches; $d_9$ may be between 1.5 and 1.6 inches; $L_{12}$ may be about 1.4 inches; the radius of curvature $R_2$ may be about 0.03 inches; and the thickness $t_2$ of the anchor member may be about 0.013 inches. Most preferably, a very small radius of curvature $R_3$ can characterize anchor joint or bend AJ2 where $R_3$ may be about 0.01 inches.

Figure 6:
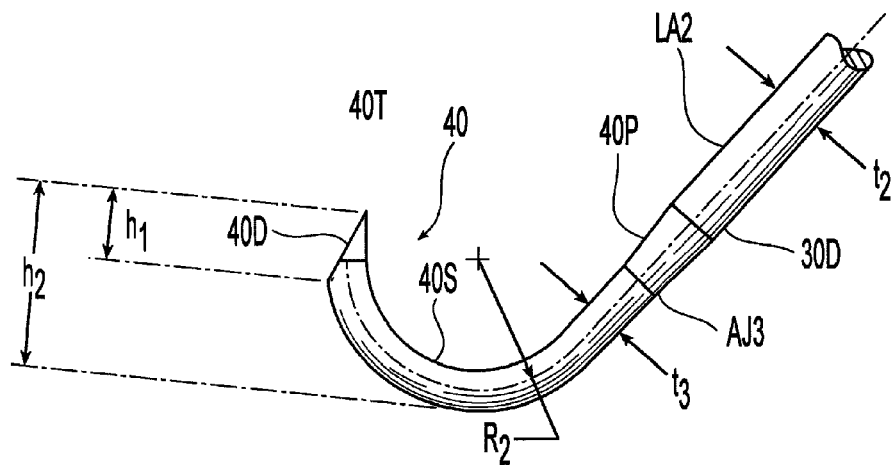
FIG. 6 is a close up side view of an anchor member hook for the filter of FIG. 1.

Referring to FIG. 6, the hook 40 may be provided with a proximal hook portion 40P and a distal hook portion 40D on which a sharpened tip 40T is provided. The hook 40 may be formed to have a thickness $t_3$. Where the hook 40 is formed from a wire having a generally circular cross section, the thickness $t_3$ may be generally equal to the outside diameter of the wire. In an embodiment, the hook thickness $t_3$ is approximately 0.8 that of the anchor thickness $t_2$. The wire may be configured to follow a radius of curvature $R_2$ whose center may be located at longitudinal distance $L_{11}$ and radial distance $d_9$ when the filter is at the temperature of a subject, as discussed above. The tip 40T may be provided with a generally planar surface 40D whose length may be approximately equal to length $h_1$. The planar surface length $h_1$ can be about 0.02 inches. The tip 40T may be located over a distance $h_2$ from a plane tangential to the curved portion 40S. The tip distance $h_2$ can be about 0.05 inches.

Figure 7:
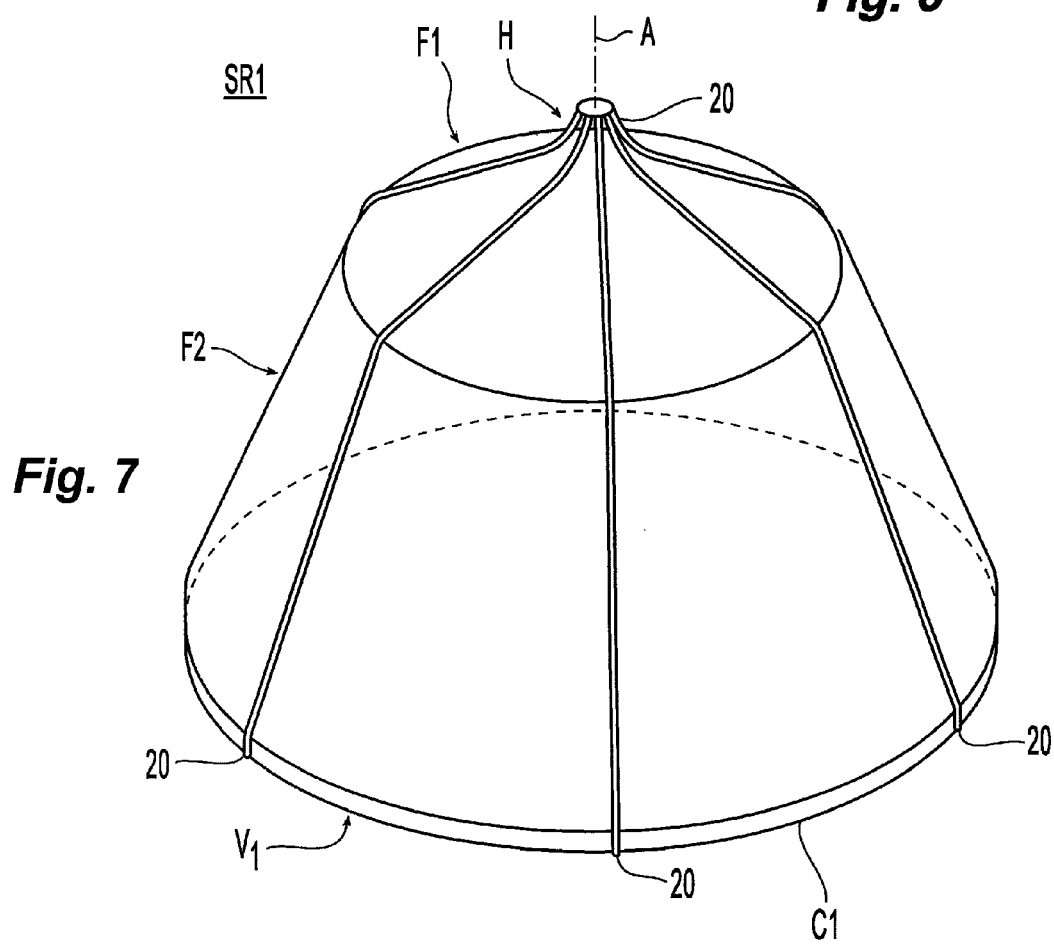
FIG. 7 is a perspective view of a volume generated by the locator members as they rotate or sweep around longitudinal axis A.
Figure 8:
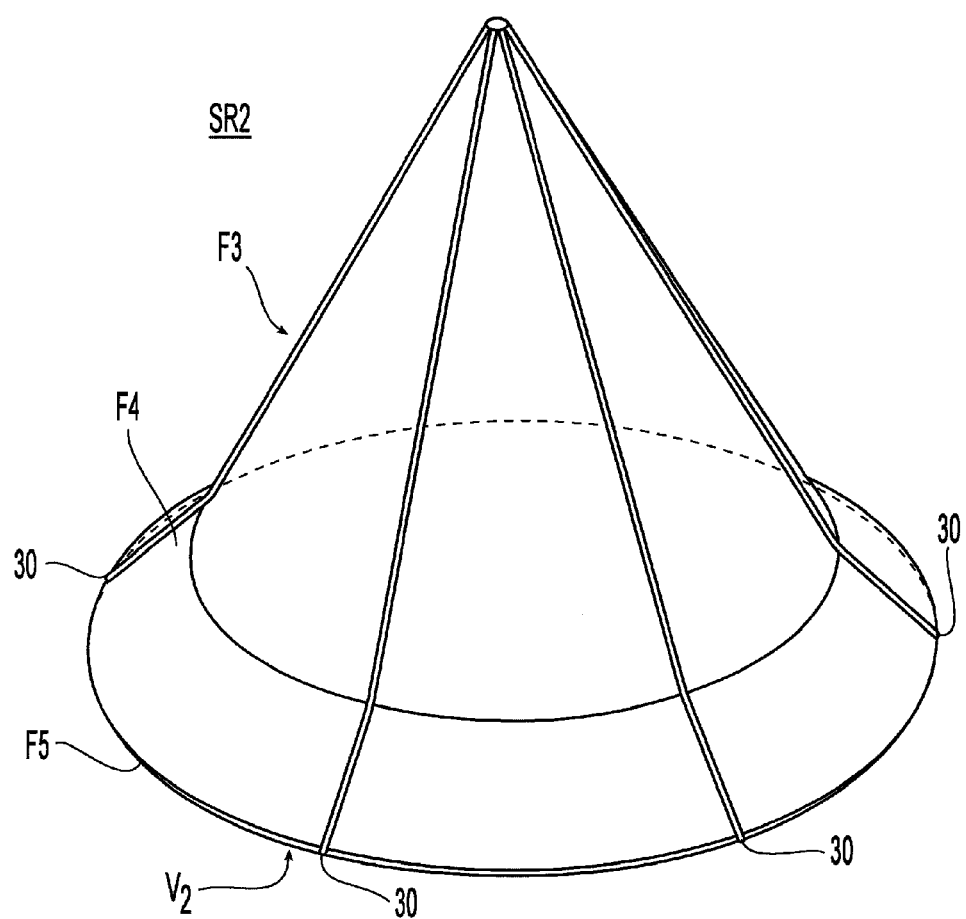
FIG. 8 is a perspective view of a volume generated by the anchor members as they rotate or sweep around the longitudinal axis A.

Referring to FIG. 7, the locators 20 are illustrated as being bounded by a first compound surface of revolution SR1 about axis A by rotating one of the locators 20 about axis A for 360 degrees. The first compound surface of revolution SR1 includes a portion of a truncated hyperboloid H, first frustum F1, second frustum F2, and cylindrical surface $C_1$. With reference to FIG. 8, the anchors 30 are illustrated as being bounded by a second compound surface of revolution SR2 about axis A by rotating one of the anchors 30 about axis A for 360 degrees. The second compound surface of revolution SR2 defined by the anchors 30 includes a third, fourth and fifth frustums F3, F4, and F5, respectively. The combination of these frustrums is the filter volume $V_3$ illustrated in FIG. 9.

Figure 9:
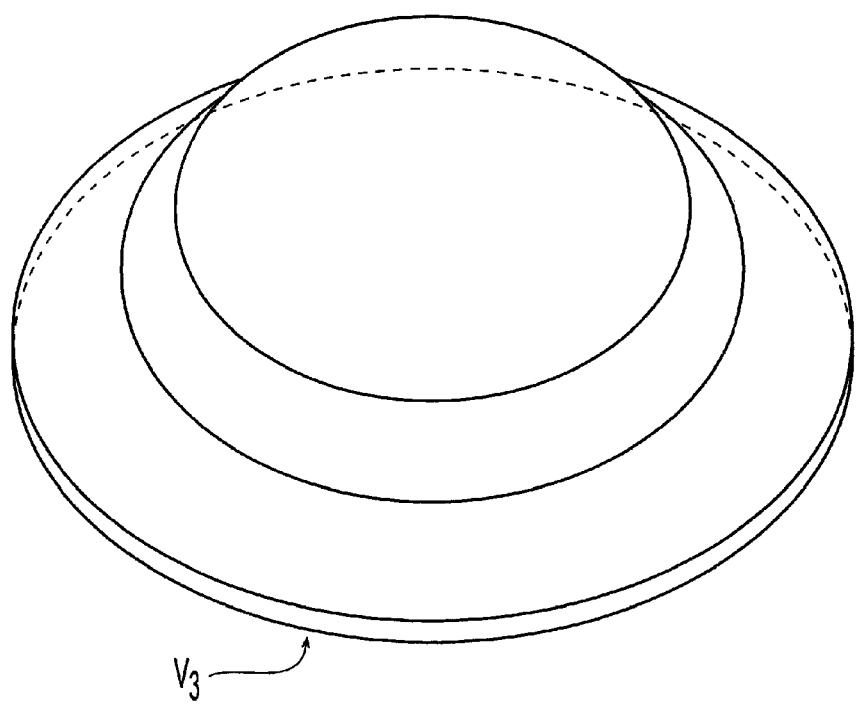
FIG. 9 illustrates the volume of the anchor member visible outside the volume of the locator member.

Several design parameters are believed to allow the preferred embodiments to achieve various advantages over the known filters. The various advantages include, for example, resisting migration of the filter 100 once installed, greater filter volume, and better concentricity with respect to the inner wall of the blood vessel. A number of design parameters may be adjusted to effect performance and fit characteristics of the filter, including, for example, the ratio of the volume $V_1$ defined by the first compound surface of revolution SR1 to the volume $V_2$ defined by the second compound surface of revolution SR2, which may be at least 0.92, preferably about 1.0, and most preferably about 0.99. Also, approximately 15% or more of the volume $V_2$ may be surrounded by the volume $V_1$, preferably at least 25% of the volume $V_2$ may be surrounded by the volume $V_1$, and most preferably, about 35% of the volume $V_2$ may be surrounded by volume $V_1$ so that the portion of volume $V_2$ that is not surrounded by volume $V_1$ (i.e., the volume of $V_2$ outside the first volume $V_1$), shown as volume $V_3$ in FIG. 9, is about 0.4 cubic inches. Also, it has been discovered that, in the preferred embodiments, as the radius $R_2$ of the hook 40 is increased, the resistance to dislodgement from a simulated blood vessel decreases. Similarly, when the radius of curvature $R_2$ is decreased, while keeping other parameters generally constant, the resistance to dislodgement from the simulated blood vessel is increased.

The material for the filter may be any suitable bio-compatible material such as, for example, polymer, memory polymer, memory metal, thermal memory material, super-elastic memory metal, linear super-elastic memory metal, metal, metal alloy, or ceramics. Preferably, the material may be Elgiloy®, and most preferably Nitinol which is a super-elastic thermal shape memory alloy.

By forming the locator 20 and anchor members 30 of a blood clot filter of a super-elastic material or Nitinol alloy material, such as Nitinol wire, transition between the martensitic and austenitic forms of the material can be achieved by temperature transitions above and below a transition temperature (referred to as the martensitic-to-austenitic transition temperature). Preferably, this transition temperature is at or below the subject's body temperature. Such controlled temperature transitions may be employed to soften and contract the Nitinol filter body to facilitate insertion into a storage tube or catheter and to subsequently expand and rigidify within a vascular or other passageway when the filter reaches body temperature. Although the filters of the various embodiments are preferably formed from a temperature-responsive shape memory material, such as Nitinol, they can also be formed of a compressible spring metal such as stainless steel or a suitable plastic.

Using a shape memory material, such as Nitinol, the deployed shapes and configurations of the filter members can be set (imprint with a memory shape) by annealing the members at high temperature while holding them in the desired shape. Thereafter, whenever the filter is in the austenitic form (i.e., at a temperature above the martensitic-to-austenitic transition temperature), the members return to the desired shape. Example methods for setting the high-temperature shape of filters are disclosed in U.S. Pat. No. 4,425,908, which is hereby incorporated by reference in its entirety.

By virtue of the characteristics of thermal shape memory material, the locator 20 and anchor members 30 can be cooled below the martensitic-to-austenitic transition temperature, and then straightened and held in a collapsed, straight form that can pass through a length of fine plastic tubing with an internal diameter of approximately two millimeters (2 mm), e.g., a No. 7 French internal diameter catheter. In its high temperature form, the filter 100 recovers to a preformed filtering shape as illustrated by FIG. 1. Alternatively, the locator and/or anchor members may be made of wires of spring metal which can be straightened and compressed within a catheter or tube and will diverge into the filter shape of FIG. 1 when the tube is removed.

In the high-temperature form of the shape memory material, the filter comprises generally coaxial first and second filter baskets or sieves, each filter basket being generally symmetrical about the longitudinal axis of the filter with both filter baskets being concave relative to the filter leading end.

Figure 2:
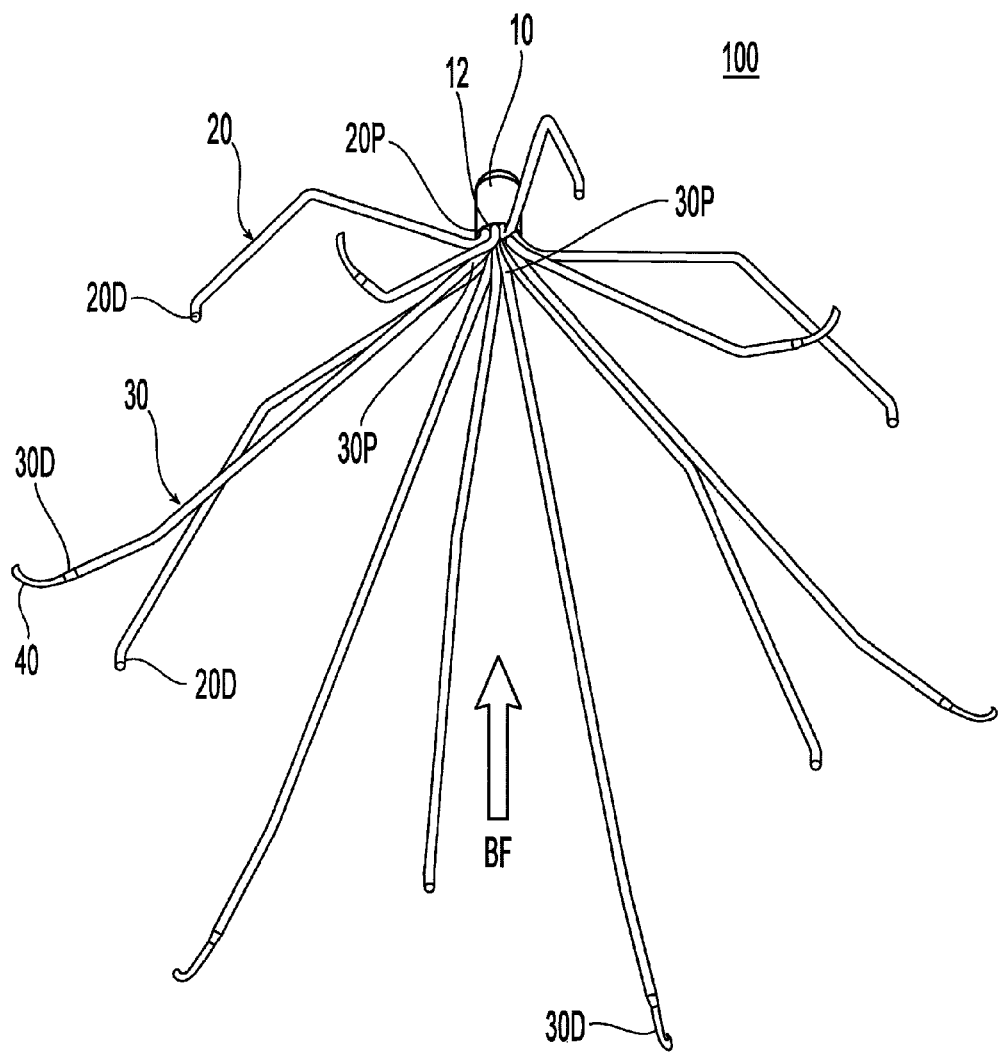
FIG. 2 is a bottom up perspective view of the filter of FIG. 1.
Figure 3:
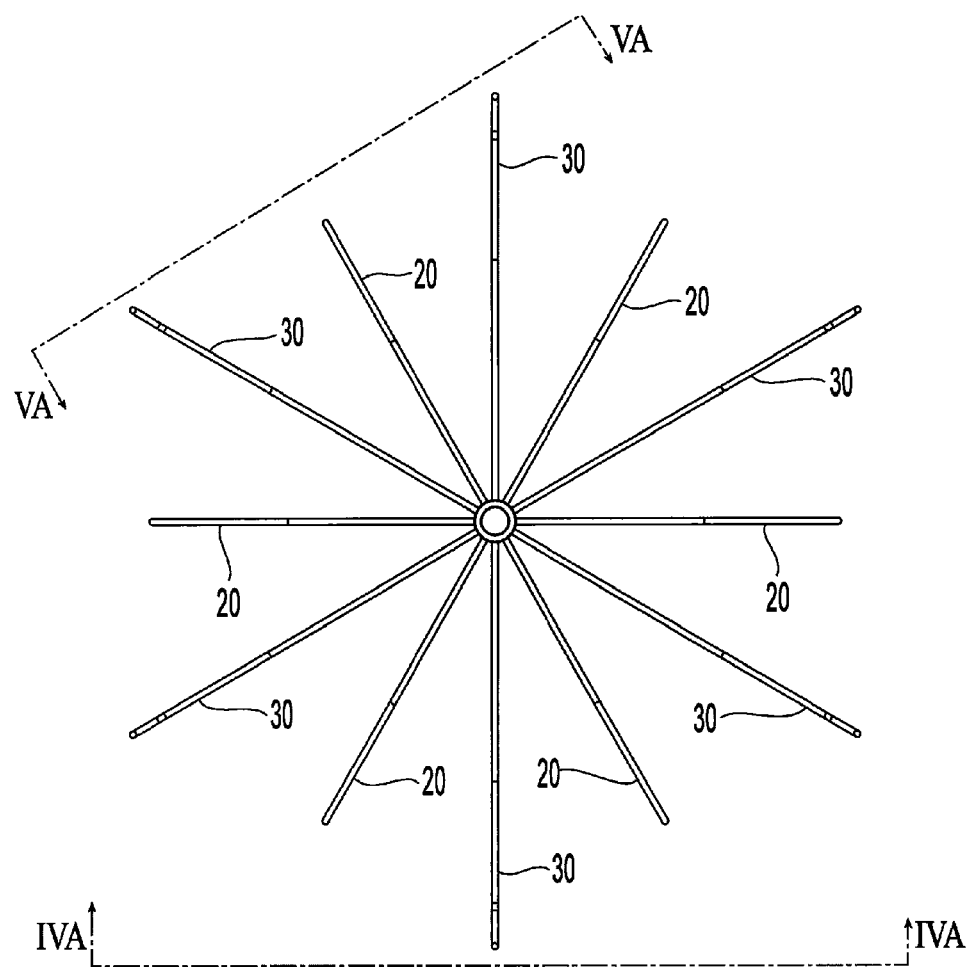
FIG. 3 is a plan end view of the filter of FIG. 1 on longitudinal axis A.

The volume $V_2$ formed by anchor members 30 constitutes the primary filter basket and can comprise up to twelve circumferentially spaced anchor members 30. Six anchor members 30 are shown in the embodiment illustrated in the figures. The anchor members may be of equal length, but alternatively or in addition to may be of different length so that the hooks 40 at the ends of the wires will fit within a catheter without becoming interconnected. The anchor members 30, in their expanded configuration illustrated in FIG. 1 (i.e., unconstrained in the high-temperature form), are at a slight angle to the vessel wall, preferably within a range of from ten to forty-five degrees, while the hooks 40 per vessel wall to anchor the filter against movement. The anchor members 30 are radially offset relative to the locator members 20 and may be positioned radially halfway between the locator members 20 and also may be circumferentially spaced by sixty degrees of arc as shown in FIG. 3. The locator members 20 form volume $V_1$, which constitutes a secondary filter basket. The combined filter volumes or baskets $V_2$ and $V_1$ can therefore provide a filter member (i.e. wire) positioned radially about the hub 10, such as at every thirty degrees of arc at the maximum divergence of the filter sections. With reference to the direction of blood flow BF shown by the arrow in FIGS. 2 and 4A, in the illustrated embodiment, the filter volume $V_2$ forms a frustum toward the hub 10 of the filter 100 while the filter volume $V_1$ forms a generally frustum-like concave sieve with its geometric center proximate the terminal end 12 of the hub 10. In the preferred embodiments, the volume $V_1$ of the surface SR1 may be between about 0.3 and about 1.1 cubic inches, preferably about 0.7 cubic inches and the volume $V_2$ of the surface SR2 may be between about 0.3 and about 1.1 cubic inches, preferably about 0.7 cubic inches.

The structure of the hooks 40 is believed to be important in resisting migration of the filter once installed while allowing for removal from the blood vessel after installation. As in the case of hooks formed on the anchor members of known permanent vena cava filters, these hooks 40 penetrate the vessel wall when the filter 100 is expanded to anchor the filter in place and prevent filter migration longitudinally within the vessel in either direction. However, when the hooks 40 are implanted and subsequently covered by the endothelium layer, they and the filter can be withdrawn without risk of significant injury or rupture to the vena cava. Minor injury to the vessel wall due to hook withdrawal such as damage to the endothelial layer or local vena cava wall puncture is acceptable.

To permit safe removal of the filter, the juncture section 40S may be considerably reduced in cross section relative to the thickness $t_2$ or cross section of the anchor member 30 and the remainder of the hook 40. The juncture section 40S may be sized such that it is of sufficient stiffness when the anchor members 30 are expanded to permit the hook 40 to penetrate the vena cava wall. However, when the hook is to be withdrawn from the vessel wall, withdrawal force in the direction of blood flow BF will cause flexure in the juncture section 40S so that the hook tip 40T moves toward a position parallel with the axis A (i.e., the hook straightens). With the hooks so straightened, the filter can be withdrawn without tearing the vessel wall while leaving only small punctures. In an embodiment, the anchor member 30 has a cross sectional area of about 0.00013 squared inches, and the hook 40, particularly the curved juncture section 40S has a cross sectional area of about 0.000086 squared inches.

With reference to FIG. 6, it will be noted that the entire hook 40 can be formed with a cross section $t_3$ throughout its length that is less than that of the locator members 20 (which have thickness $t_1$) or anchor members 30 (which have thickness $t_2$). As a result, a sufficient axial withdrawal force will tend to straighten the hook 40 over its entire length, i.e., the hook will deform from its initial radius of curvature to a larger radius of curvature. This elasticity in the hook structure prevents the hook from tearing the vessel wall during withdrawal.

As previously indicated, while it is possible that the filter could be made from ductile metal alloys such as stainless steel, titanium, or Elgiloy®, it is preferable to make it from Nitinol. Nitinol is a low modulus material that allows the locator and anchor members of the device 100 to be designed to have low contact forces and pressures while still achieving sufficient anchoring strength to resist migration of the device.

The force required to cause opening of the hooks 40 can be modulated to the total force required to resist filter migration. This is accomplished by changing the cross sectional area or geometry of the hooks, or by material selection, as discussed above.

In addition to temperature sensitivity, when in the high temperature austenitic state, Nitinol is also subject to stress sensitivity that can cause the material to undergo a phase transformation from the austenitic to the martensitic state while the temperature of the material remains above the transition temperature. By reducing the cross sectional area of a portion or all of the hooks 40 relative to that of the anchor members 30 or locator members 20, the areas of reduced cross section will be subject to stress when a longitudinal force is applied to the hub 10 in the direction of blood flow BF (i.e., towards the hub 10 of the filter) such as to remove the filter. Under this stress, the reduced cross section portions of the hooks may straighten while transitioning to the martensitic state, thereby becoming super elastic. Regardless of whether formed of Nitinol, Elgiloy®, spring metal or plastic, the hooks 40 are preferably designed to bend toward a substantially straight configuration when a specific hook migration force is applied and spring back to their original shape once the hook migration force is removed.

The force or stress that is required to deform the hooks 40 can be correlated to the force applied to each hook of the device when it is fully occluded and the blood pressure in the vessel is allowed to reach 50 millimeters of mercury (mmHg) in a test stand. The test stand (not shown) can be configured to have a length of tubing (with various internal diameters) to allow a filter to be suitably attached thereto. The tubing is connected to another tubing having a terminal end exposed to ambient atmosphere and marked with gradations to indicate the amount of pressure differential across the filter, which is related to the force being applied to each locator of the filter 100. This force is approximately at least 70 grams on each anchor of a six-anchor device for at least 50 mmHg pressure differential in a 28 mm vessel. The desired total migration resistance force for the filter is believed to be approximately 420 grams for the embodiment of a vena cava filter for an adult human subject, and more anchor members 30 with hooks 40 can be added to lower the maximum migration force for each hook. The load on the filter would be correspondingly smaller in vessels of smaller diameter. The design object is to have the hooks 40 perform as an anchoring mechanism at a predetermined filter migration resistance force within a range of about 10 mmHg up to about 150 mmHg. Having maintained its geometry at a predetermined filter migration resistance force within this range, the hook 40 preferably begins to deform in response to a higher force applied in the direction of the hub, i.e., the filter trailing end TE (FIG. 1) with respect to blood flow, and is believed to release at a force substantially less than that of known filters. It is the ability of the hook to straighten somewhat that allows for safe removal of the preferred embodiment filters from the vessel wall.

After the filter 100 has remained in place within a blood vessel in excess of two weeks, the endothelium layer will grow over the hooks 40. Since these hooks 40, however, substantially straighten when subjected to a withdrawal force in the direction of the hub (i.e., toward the trailing end TE), the filter can be removed leaving only six pinpoint lesions in the surface of the endothelium. To accomplish this, a catheter such as, for example, the unit described and shown in U.S. Pat. No. 6,156,055, which is hereby incorporated by reference in its entirety, or similar retrieval unit is inserted opposite the direction of blood flow BF over the hub 10 and into engagement with the locator members 20. While the hub 10 is held stationary, the catheter may be moved downwardly, forcing the locator members 20 to fold toward the axis A, and subsequently engaging the anchor members 30 and forcing them downwardly thereby withdrawing the hooks 40 from the endothelium layer. Then the hub 10 may be drawn into the catheter to collapse the entire filter 100 within the catheter. When the filter is formed from shape memory material, cooling fluid (e.g., chilled saline) may be passed through the catheter during these steps to aid in collapsing the filter.

The primary objective of the hooks 40 is to ensure that the filter does not migrate during normal respiratory function or in the event of a massive pulmonary embolism. Normal inferior vena cava (IVC) pressures are believed to be between about 2 to about 5 mmHg. An occluded IVC can potentially pressurize to 35 mmHg (or more) below the occlusion. So to ensure filter stability, a filter may be designed to resist a migration force of 50 mmHg across the filter 100. When a removal pressure is applied to the filter that is greater than at least 50 mmHg, the hooks 40 will deform and release from the vessel wall. The pressure required to deform the hooks can be converted to force by the following calculations.

Since 51.76 mmHg=1.0 pounds per square inch (psi),
50 mmHg=0.9668 psi.
For a 28 mm vena cava:

$$A = \frac{\pi}{4}(28)^2 \text{ mm}^2 = 615.4 \text{ mm}^2 = 0.9539 \text{ inches}^2$$

Migration force is calculated by:

$$P = \frac{F}{A} \quad F = P \times A$$

0.9668 psi×0.9539 inches$^2$=0.9223 pounds=418.7 grams.

It should be noted that as the vena cava diameter increases, so does the force required to resist at least 50 mmHg of pressure.

Depending on the number of filter hooks 40, the required strength of each hook can be calculated. For a device that has six hooks:

$$\text{Hook Strength} = \frac{\text{Filter Migration Resistance Force}}{\text{Number of Hooks}} = \frac{418.7}{6} = 69.7 \text{ grams.}$$

In other words, each hook must be capable of resisting approximately at least 70 grams of force for the filter 100 to resist at least 50 mmHg pressure gradient in a 28 mm diameter vessel.

To prevent excessive vessel trauma each individual hook preferably has a low hook strength. By balancing the number hooks and the individual hook strength, minimal vessel injury can be achieved while still maintaining the at least 50 mmHg pressure gradient criteria, or some other predetermined pressure gradient criteria within a range of from 10 mmHg to 150 mmHg.

Referring to FIG. 4A, the anchor members 30 may be angled outwardly from the anchor joint or bend AJ1 adjacent to but spaced from the outer end of each anchor member 30. When the anchor members 30 are released from compression in a catheter or other tube into a body vessel, this bend in each anchor member insures that the hooks 40 are, in effect, spring loaded in the tube and that they will not cross as they are deployed from the tube. Since the anchor members 30 are angled outwardly, the hooks 40 are rapidly deployed outwardly as the insertion tube is withdrawn.

A filter delivery unit (not shown) such as, for example, the unit described in U.S. Pat. No. 6,258,026, which is hereby incorporated by reference in its entirety, is adapted to deliver the filter 100 through a catheter or delivery tube to a generally centered position within a body vessel, as described in further detail in the above mentioned patent. Further methods of delivering a blood filter according to the various embodiments are disclosed in PCT International Application No. PCT/US06/17890, entitled "Embolus Blood Clot Filter and Delivery System," filed on May 9, 2006, which is hereby incorporated by reference in its entirety.

Figure 10:
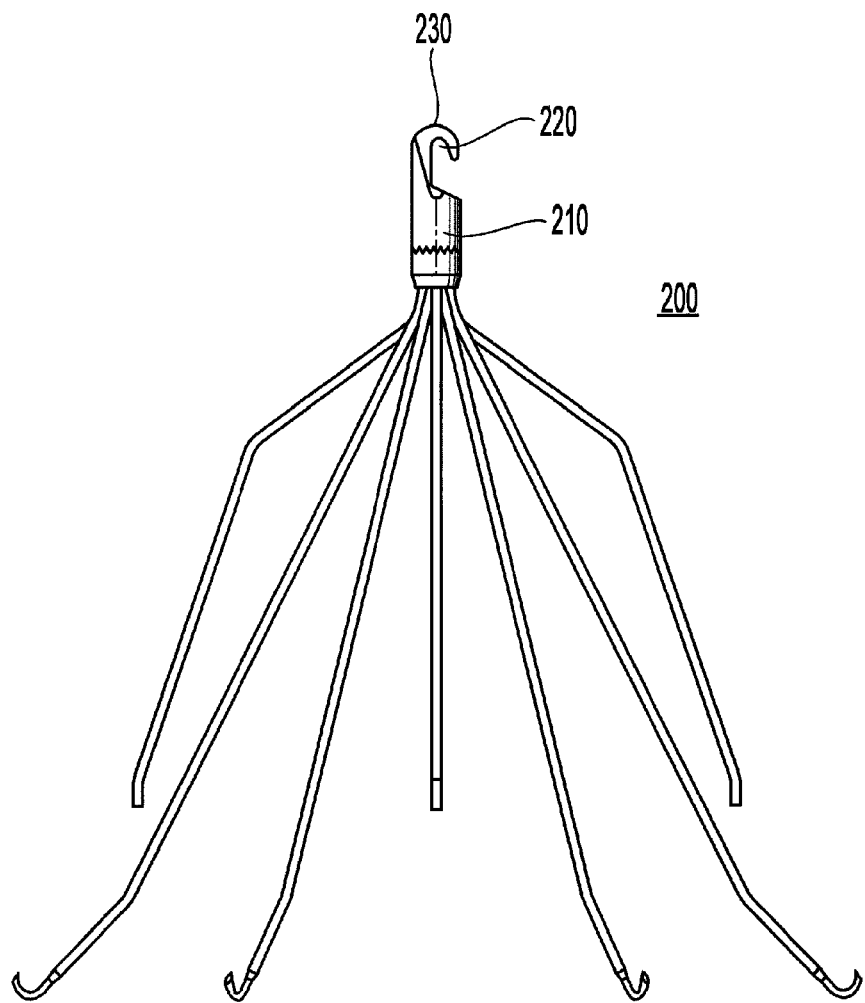
FIG. 10 illustrates an embodiment having a filter retrieving hook portion.
Figure 11:
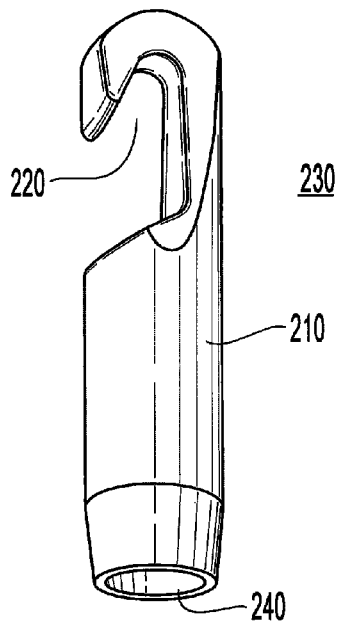
FIGS. 11-14 are detailed views of the retrieving hook for a filter according to FIG. 10.
Figure 12:
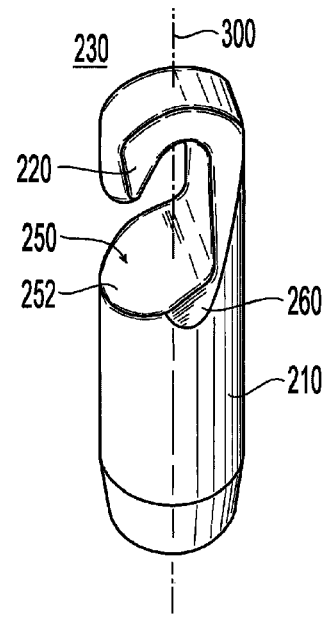
Figure 13:
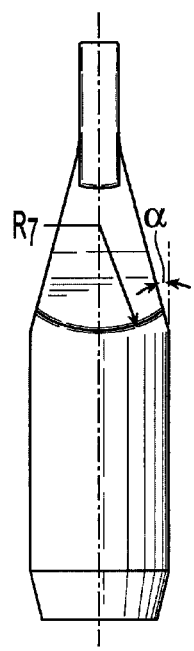
Figure 14:
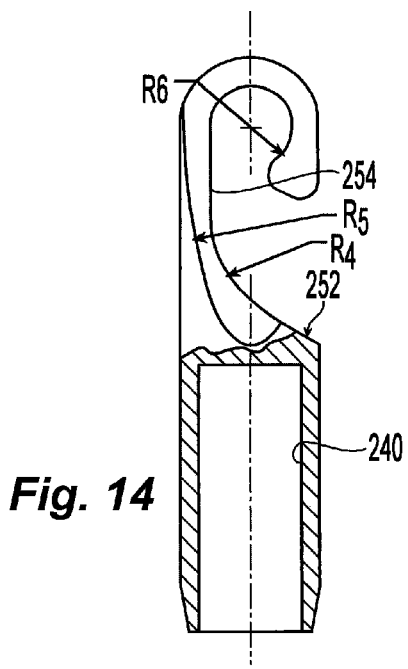

Alternatively or in addition to, the hub 10 can include a retrieving end fitting 230 can be provided as part of filter device 200, as shown, for example, in the filter 200 of FIG. 10. More specifically, the filter device 200 preferably includes a hub 210 with a retrieving tip embodied as a retrieving hook 220. The hook 230 is configured for use by a snaring device to retrieve the filter 200 from a subject. Referring to FIGS. 11 and 12, the retrieving hook 230 can be formed as a monolithic member with the hub 210. Alternatively, the hook may be provided as a separate member joined to the hub 210 by a suitable technique, such as, for example, laser welding, plasma welding, brazing, welding, soldering, or bonding. In a preferred embodiment, the tip 230 can be a machined billet member with a blind bore 240 formed through a portion of the hub 210. The hook 220 preferably includes ramped surfaces 250 and 260 that are believed to be advantageous in allowing the filter 200 to be retrieved without binding at the catheter opening due to an offset entry position of the filter 200. In other words, there may be circumstances during removal procedures where the axis 300 of the hook 230 is not generally parallel or aligned with a longitudinal axis of the catheter retrieving device. In such cases, it is believed that the greater the retention force, the greater the likelihood of the hook being snagged on the catheter inlet opening thereby complicating the filter retrieval process. By virtue of the ramps 250 and 260, it is believed that binding or snagging is substantially reduced. In particular, as shown in FIGS. 13 and 14, the ramp 250 includes a radius of curvature $R_4$ coupled to first flat portion 252 and second flat portion 254. The flat portion 254 can be coupled to the hook portion 220 which has a radiused surface $R_6$. As shown in FIG. 14, the first flat portion 252 is coupled to another radiused portion $R_7$. It should be noted that the drawings provided herein are to scale relative to every part illustrated in each drawing.

A range of values may be used for the aforementioned dimensional parameters in order to provide a retrieval hook 230 that is capable of retaining portions of the locator members 20 and anchor members 30 within blind bore 240. For example, a smaller filter may have smaller dimensions so that the retrieval hook 230 does not present undue blockage in the vein, than a filter intended to be placed in a large vein or vessel, such as an adult vena cava or femoral vein.

Figure 23A:
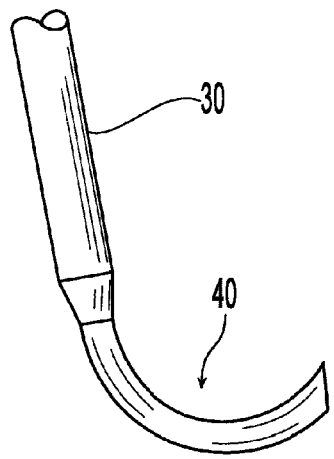
FIGS. 23A and 23B are detailed views of a hook portion of the filter of FIG. 22.
Figure 23B:
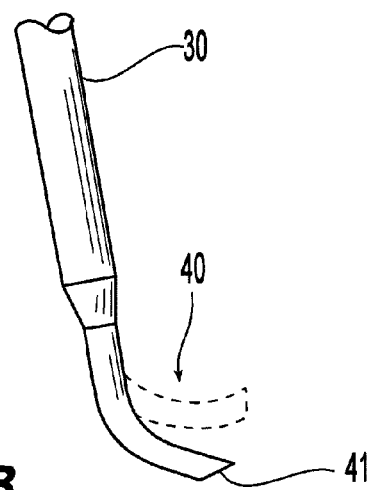

As longitudinal force 8 is applied to the anchor members 30 and the hooks 40 deform as illustrated, for example, in FIG. 23, the hooks 40 will tend to move both tangential to and perpendicular 9 to the vessel wall 6. To facilitate removal, a sharp edge or blade 50, as illustrated in FIG. 15, can be provided on portions of the hooks 40 and anchor members 30 which may be covered by endothelial overgrowth 7.

For the purpose of the various embodiments, a sharp edge 50 is an edge that is sufficiently narrow so as to either cut or slice (e.g., a blade) through endothelial tissue, or to present a focused line of stress to the tissue so the endothelial tissue preferentially tears along the edge, inducing clean tearing without traumatic ripping of the tissue. Where, for example, the anchor member 30 and hook 40 are thin wires, with a diameter of approximately 0.02 inch or less. Thus, the sharp edge need be only slightly narrower in cross section (i.e., characterized by a smaller radius of curvature) than the anchor member 30 and hook 40 in order to cause the desired preferential tearing of the endothelial tissue. Further, the sharp edge itself may itself be curved or rounded, provided the radius of curvature of the edge is sufficiently narrower than that of the hook/anchor wires to induce preferential tearing of tissue. Providing a sharp edge or blade 50 permits the hook/anchor wires to pass cleanly through the endothelial overgrowth 7, thereby preventing traumatic rupturing or ripping of the tissue layer from the vessel wall 6.

Figure 15:
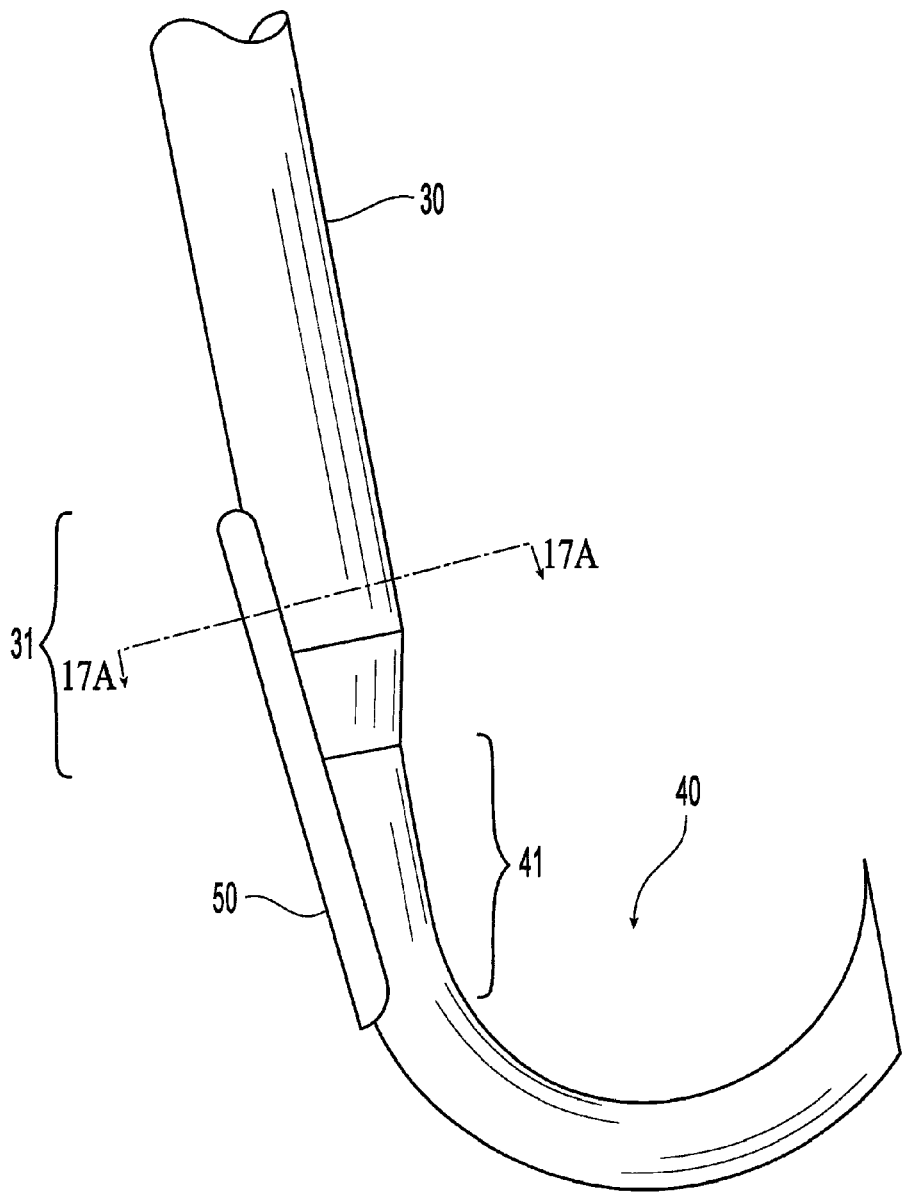
FIG. 15 is a detailed perspective view of a hook according to another embodiment.
Figure 24:
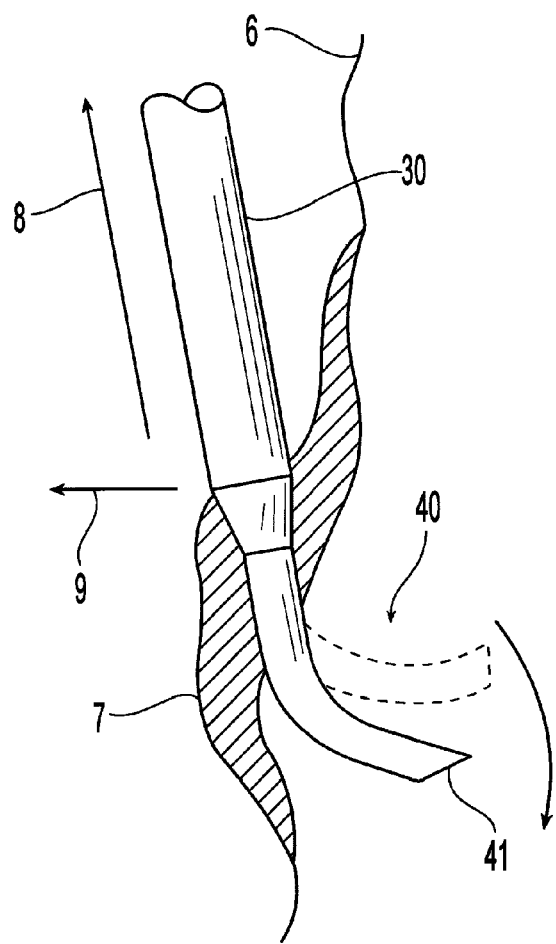
FIG. 24 is a detailed view of a hook portion of the filter of FIG. 22 embedded in a blood vessel with endothelial overgrowth.

In the various embodiments, the sharp edge or blade 50 may extend from a shank portion 41 of the hook 40 through the anchor's lower portion 31, as illustrated in FIG. 15. This is the portion of the anchor member most likely to be covered by endothelial overgrowth as illustrated in FIG. 24. The sharp edge 50 need not be limited to the portions 41 and 31 where endothelial overgrowth may occur, and instead may extend for the entire length of the anchor, as this may facilitate manufacturing of the anchor members. As illustrated in FIG. 15, the sharp edge or blade 50 may be oriented so the edge 50 projects toward the filter's longitudinal axis, and thus is positioned on the circumference of the anchor 30 and hook shank 41 opposite the extension of the hook 40 away from the centerline of the anchor. This is because the anchor 30 and hook shank 41 will be pushed toward the filter longitudinal access as the hook deflects, as illustrated in FIG. 24. In various embodiments of the filter, a similar sharp edge or blade may also be included on locator members 20, and in particular on the interior side, i.e., projecting toward the filter longitudinal axis, of the portion of locators that contact the blood vessel wall (e.g., the distal locator end 20D illustrated in FIGS. 1-2), since endothelial overgrowth may occur there as well.

A number of configuration embodiments for the sharp edge or cutting blade 50 structures are possible, some examples of which are illustrated in FIGS. 16-20. Embodiments are not limited to those shown and described herein since other configurations are within the scope of the claims.

Figure 16:
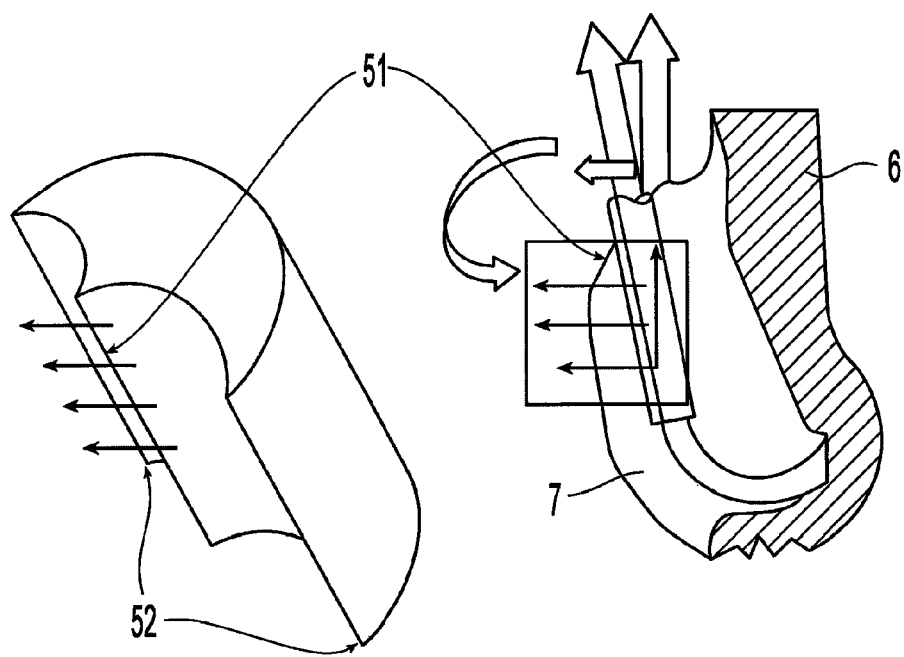
FIG. 16 is a detailed perspective view of a hook according to an embodiment.

Referring to FIG. 16, more than one sharp edge 51, 52 may be employed in order to address the possibility that filter removal forces can result in rotational as well as tangential and perpendicular force elements. Also, the hook 40 may have twisted about the long axis of the anchor member 30 during delivery or while in service so that the hook engages the vessel wall at an oblique angle. As a consequence, the perpendicular force may be applied to the endothelial overgrowth along an edge that is at an angle to the plane of the hook (i.e., at an angle to a radian from the blood vessel's centerline). In the embodiment illustrated in FIG. 16, a first cutting edge 51 oriented opposite to the projection of the hook 40 is flanked on either side by supplemental sharp edges 52. This embodiment will present a sharp edge 51 or 52 to the endothelial overgrowth whether the hook is oriented at a rotational angle to the vessel wall 6 (i.e., oriented at an angle to a radian from the blood vessel's centerline) or twists in either direction during the retraction process.

Figure 17A:
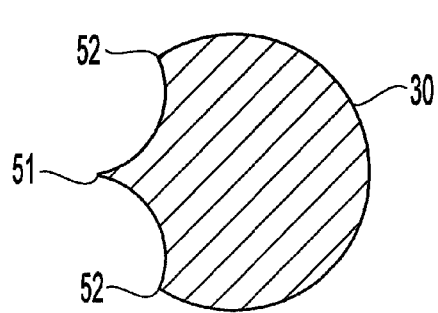
FIG. 17A is a cross sectional view of a portion of a hook according to an embodiment.
Figure 17B:
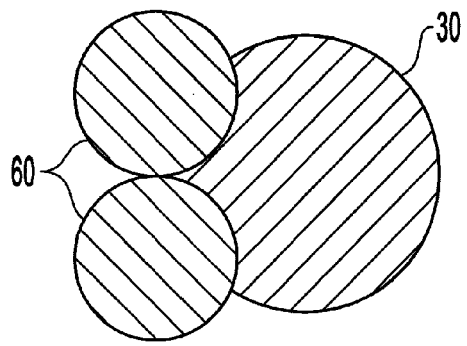
FIG. 17B is a diagram illustrating a method of fabricating the portion of the hook illustrated in FIG. 17A.

FIG. 17A provides a cross sectional view of the embodiment illustrated in FIG. 16 and along line 17A-17A in FIG. 15. This triple sharp edge embodiment may be formed by removing two cylindrical portions 60 out of the anchor 30 and hook shank 41, as illustrated in FIG. 17B. The cylindrical portions 60 may be removed by machining, for example, by electrical discharge machining (EDM). Alternatively, the wire used to form the anchor and hook may be drawn through a die that yields such a cross section.

Figure 18:
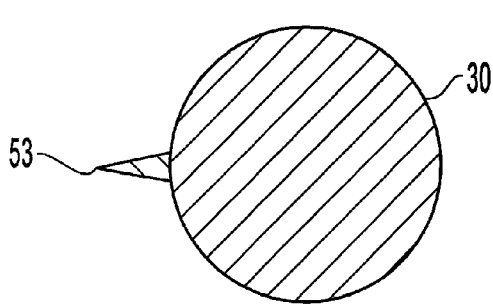
FIG. 18 is a cross sectional view of a portion of a hook according to another embodiment.

Referring to FIG. 18, another embodiment features a single blade 53 fashioned on the anchor member 30. This blade 53 may be formed by removing a portion of the filter member through machining, e.g., EDM, polishing or etching, or may be formed by welding additional material, such as a blade, onto the anchor member 30.

Figure 19:
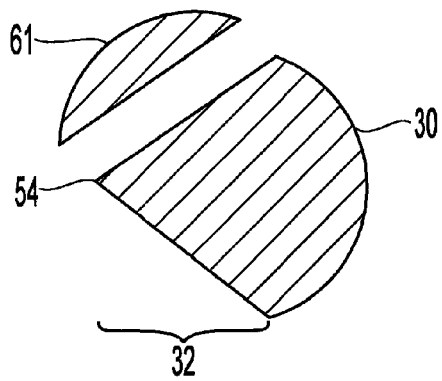
FIG. 19 is a cross sectional view of a portion of a hook according to another embodiment.

Referring to FIG. 19, a sharp edge 54 may be formed by removing portions 61 of the anchor member 30, such as by machining, polishing, etching or grinding, to render a generally triangular cross section portion 32. This embodiment may have fabrication advantages over those illustrated in FIGS. 17A, and 18 given its simple configuration.

Figure 20:
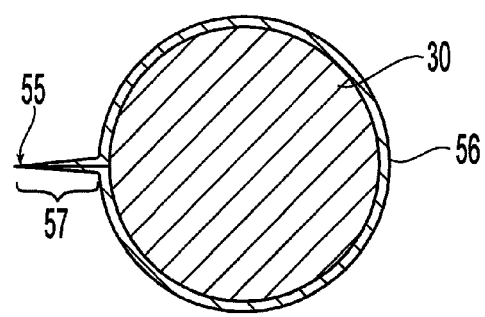
FIG. 20 is a cross sectional view of a portion of a hook according to another embodiment.

Referring to FIG. 20, a sharp edge 55 may be formed by wrapping a thin metal or hard plastic foil 56 around the anchor member 30 and bonding the edge portions 57 together. A thin foil 56 will form a sharp blade 55 where the edges meet. The resulting edge may be further sharpened by a brief etching process. Foil 56 may be bonded to the anchor member 30 by a number of known methods, including, for example, swagging, brazing, welding, and bonding with biocompatible adhesives. This embodiment may have fabrication advantages over the embodiments illustrated in FIGS. 17A-19 since the foil may be applied after the anchor 30 and hook 40 have been formed, and just over the portion of the anchor and hook where endothelial overgrowth is expected.

Figures 21A, 21B, 21C:
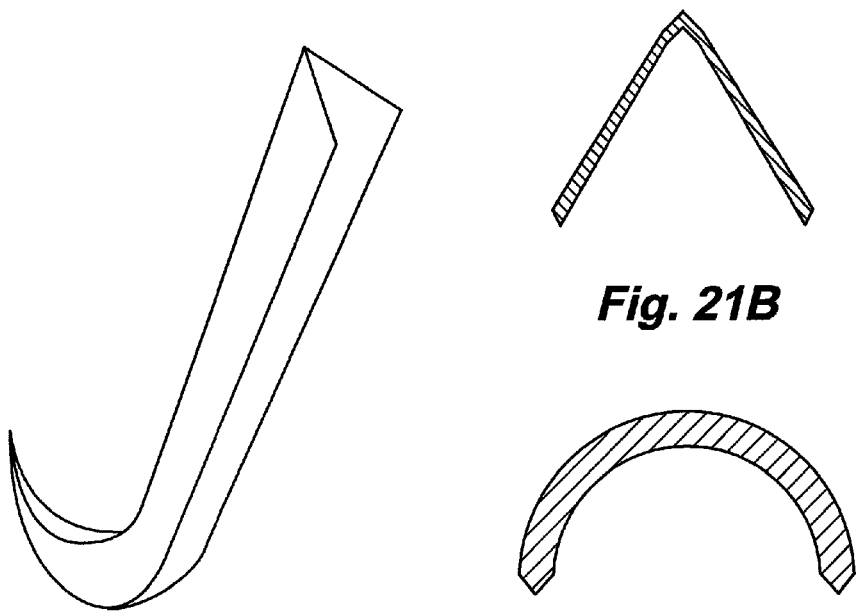
FIGS. 21A-C show cross sectional views of a portion of a hook according to other embodiments.
Figure 22:
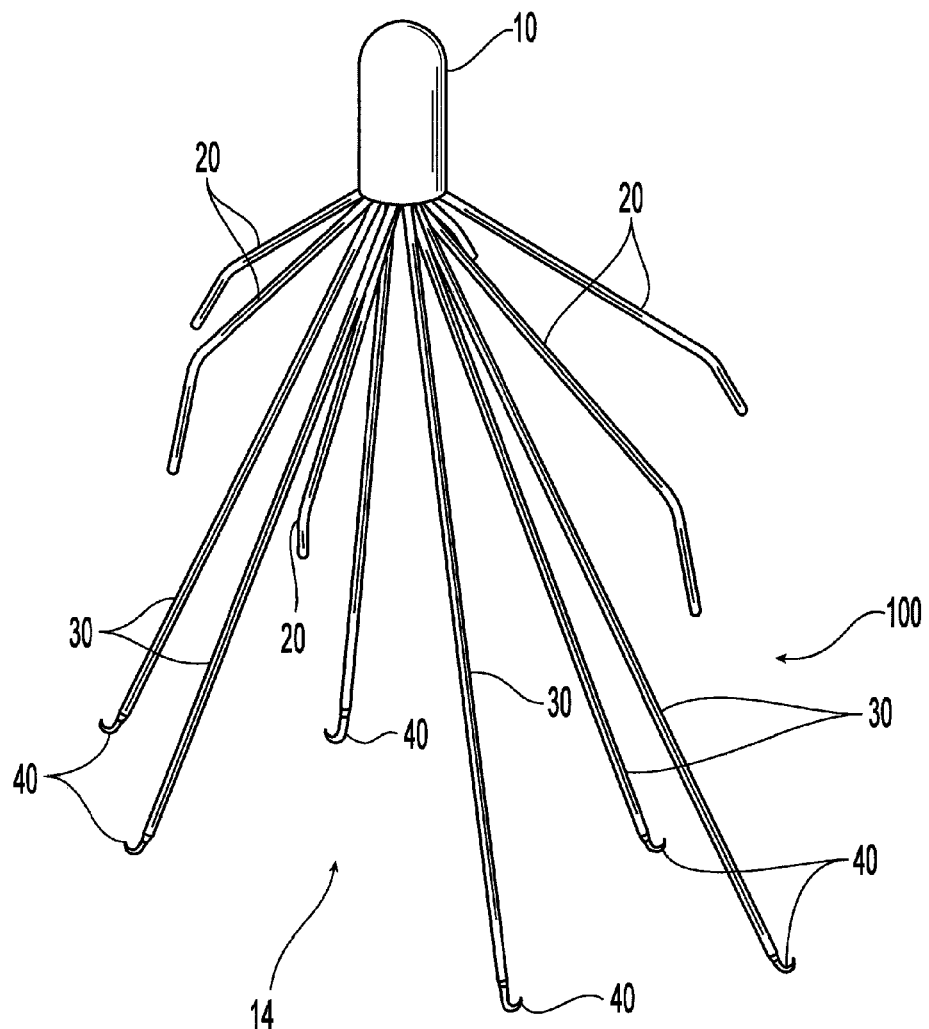
FIG. 22 is a perspective view of a prior art blood filter.

Referring to FIGS. 21A-21C, at least one sharp edge can be formed by folding a generally planar member along a crease. As shown in FIGS. 21A and 21B, there can be three sharp edges formed by this technique where the edges in cross section delineate a triangle, as illustrated in FIG. 21B. Alternatively, the folding can be accomplished by curving the planar member into an arch and sharpening the terminal edge surface, as illustrated in FIG. 21C.

Although the preferred embodiments have been shown and described in relation to the filter of FIG. 1, other filters can also be utilized in conjunction with the sharp edge wherever portions of such filters are in contact with the vessel wall. For example, the sharp edge can be provided for the overlapping loops of the filter shown and described in U.S. Pat. No. 4,425,908, which is hereby incorporated by reference in its entirety. The sharp edges can also be provided on the outermost perimeter in contact with tissue for the filter shown and described in U.S. Pat. No. 6,443,972, which is also hereby incorporated by reference in its entirety. Commercially available filters in which the sharp edge described herein can be utilized for portions of such filter in proximity to vessel wall tissue include but are not limited to the Greenfield® Filter, VenaTech® Filter, Gunther Tulip® Filter, TrapEase® or OptEase®.

While the present invention has been disclosed with reference to certain preferred embodiments, numerous modifications, alterations, and changes to the described embodiments are possible without departing from the sphere and scope of the present invention. Accordingly, it is intended that the present invention not be limited to the described embodiments, but that it have the full scope defined by the language of the following claims, and equivalents thereof.

What is claimed is:

1. A removable filter to be placed in a flow of blood through a blood vessel having a wall, the filter comprising:
   a) a head having proximal and distal end portions and a central longitudinal axis;
   b) a plurality of filter members extending from the head in generally one direction that is distally of the head, at least some of the filter members having a first larger diameter and a distal end, a tapered portion affixed to said distal end and a hook attached to said tapered portion opposite said distal end, each hook including a curved section extending distally away from said tapered portion and laterally away from said central longitudinal axis, said curved portion having a radius of curvature larger than said first diameter, said hook terminating at a hook free end that is spaced away from the distal end of the filter member with a gap in between said filter member distal end and said hook free end, said hook defining a plane;

c) wherein said hook is of a second smaller diameter when compared to the first larger diameter of said filter member; and d) a sharp edge spanning at least a portion of at least one of the filter members and extending to said tapered portion, said sharp edge extending from said tapered portion toward said curved portion but terminating before extending over a majority of the curved portion of the hook so that the hook curved portion is able to straighten during removal from the wall of the blood vessel, said sharp edge being in said plane.

2. The filter according to claim 1, wherein the sharp edge extends over a portion of the at least one filter member adjacent to a wall of the blood vessel when the filter is positioned in the blood vessel.

3. The removable filter of claim 1 wherein the sharp edge extends above and below the tapered section.

4. The filter according to claim 1, wherein the at least one filter member also includes a locator member.

5. The filter according to claim 1, wherein the hook further includes a second sharp edge over at least a portion of the filter member.

6. The filter according to claim 5, wherein the hook further includes a third sharp edge over at least a portion of the filter member.

7. The filter according to claim 1, wherein the sharp edge projects toward a longitudinal axis of the filter.

8. The filter according to claim 1, wherein the sharp edge is formed by removing a portion of the filter member.

9. A filter to be placed in a blood vessel having a wall, the filter comprising:

a) a hub disposed along a longitudinal axis, the hub having proximal and distal end portions;

b) a plurality of legs branching away from the hub in generally one direction that is distally of the hub, each leg including a leg distal end portion of a first, larger diameter and a tapered portion;

c) a hook that (i) is configured to penetrate a wall of the blood vessel, (ii) is spaced along the longitudinal axis from the hub, and (iii) has a curved portion that curves radially away from the longitudinal axis;

d) wherein said hook extends distally of said tapered portion, said hook defining a plane and having a free end spaced radially away from the leg distal end and radially away from said longitudinal axis a first radial distance, there being a gap in between said hook free end and said leg distal end that is larger than said first larger diameter;

e) a blade extending above and below the tapered portion over both a portion of the leg distal end portion and over at least part of the hook;

f) wherein the hook curved portion has a reduced diameter distally of said leg distal end portion so that said hook curved portion is able to straighten during removal from the blood vessel wall;

g) a plurality of locator members branching from the hub; and h) wherein said blade occupies said plane.

10. The filter according to claim 9, wherein each locator member includes:

a base portion proximate the hub;

a first portion that extends from the base portion and along a first axis;

a second portion that extends from the first portion and along a second axis, which is distinct from the first axis; and a tip portion that extends from the second portion and along a tip axis, which is distinct from the first and second axes, the tip portion (i) is configured to engage the wall of the blood vessel, (ii) is spaced along the longitudinal axis from the hub, and (iii) is radially spaced from the longitudinal axis a second distance, which is less than the first radial distance.

11. The filter according to claim 10, wherein each locator member further includes on the tip portion a sharp edge projecting toward the longitudinal axis.

12. A filter to be placed in a blood vessel, the filter comprising:

a) a hub disposed along a longitudinal axis, the hub having proximal and distal end portions;

b) a plurality of legs branching away from the hub, each leg including a leg proximal end attached to the hub and a leg distal end having a first diameter and a tapered portion;

c) a hook that (i) is configured to penetrate a wall of the blood vessel, (ii) is spaced along the longitudinal axis from the hub, and (iii) has a hook curved portion that curves radially away from the longitudinal axis a first distance;

d) wherein said hook curved portion extends distally of said tapered portion, said hook curved portion defining a plane and having a first hook end attached to tapered portion and a second hook end that is a free end spaced radially away from the leg distal end and radially away from said longitudinal axis, there being a gap in between said hook free end and said leg distal end that is larger than said first diameter;

e) a blade extending over both the tapered portion of the leg and over a portion of the hook, wherein the blade does not extend over a majority of the hook so that the hook curved portion that extends distally of the blade is able to straighten during removal from the blood vessel wall; and f) a plurality of locator members branching from the hub.

13. A removable filter to be placed in a flow of blood through a blood vessel, the filter comprising:

a) a head having proximal and distal end portions and a central longitudinal axis;

b) a plurality of filter members extending distally of the head, at least some of the filter members having a first diameter and a distal end;

c) a tapered portion affixed to said filter member distal end;

d) a hook shaped anchor attached to said tapered portion opposite said filter member distal end;

e) each hook shaped anchor including a hook curved portion extending distally away from said tapered portion and laterally away from said central longitudinal axis, said hook curved portion having a radius of curvature, said hook shaped anchor terminating at a hook free end that is spaced away from the distal end of the filter member with a gap in between said filter member distal end and said hook free end, said hook curved portion defining a plane;
f) wherein said hook curved portion is of a reduced diameter when compared to the diameter of said filter member;
g) a blade spanning over at least a portion of at least one of the filter members and above and below the filter member distal end; and
h) said blade not extending from said tapered portion along the entire hook curved portion so that the hook curved portion that extends distally of the blade is not reinforced by the blade and is able to straighten during removal from the blood vessel wall.

* * * * *